US009772328B2

(12) United States Patent
Stein et al.

(10) Patent No.: US 9,772,328 B2
(45) Date of Patent: *Sep. 26, 2017

(54) BIMOLECULAR PROTEASE-BASED BIOSENSOR

(71) Applicant: The University of Queensland, St. Lucia, Queensland (AU)

(72) Inventors: Viktor Stein, St. Lucia (AU); Kirill Alexandrov, St. Lucia (AU)

(73) Assignee: The University of Queensland, Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/021,494

(22) PCT Filed: Sep. 12, 2014

(86) PCT No.: PCT/AU2014/000896
§ 371 (c)(1),
(2) Date: Mar. 11, 2016

(87) PCT Pub. No.: WO2015/035452
PCT Pub. Date: Mar. 19, 2015

(65) Prior Publication Data
US 2016/0223529 A1    Aug. 4, 2016

(30) Foreign Application Priority Data

Sep. 12, 2013  (AU) ................. 2013903499

(51) Int. Cl.
| | |
|---|---|
| *G01N 33/542* | (2006.01) |
| *C07K 19/00* | (2006.01) |
| *C12N 9/48* | (2006.01) |
| *C07K 14/00* | (2006.01) |
| *C07K 14/005* | (2006.01) |
| *C07K 14/47* | (2006.01) |
| *C07K 16/00* | (2006.01) |
| *C12N 7/00* | (2006.01) |
| *C12N 9/50* | (2006.01) |
| *C12N 9/90* | (2006.01) |
| *G01N 33/58* | (2006.01) |

(52) U.S. Cl.
CPC .......... *G01N 33/542* (2013.01); *C07K 14/00* (2013.01); *C07K 14/005* (2013.01); *C07K 14/4728* (2013.01); *C07K 16/00* (2013.01); *C07K 19/00* (2013.01); *C12N 7/00* (2013.01); *C12N 9/48* (2013.01); *C12N 9/506* (2013.01); *C12N 9/90* (2013.01); *G01N 33/582* (2013.01); *C07K 2319/50* (2013.01); *C07K 2319/61* (2013.01); *C07K 2319/70* (2013.01); *C12N 2770/34011* (2013.01); *C12Y 304/22044* (2013.01); *C12Y 502/01008* (2013.01); *G01N 2333/08* (2013.01); *G01N 2333/185* (2013.01); *G01N 2333/4727* (2013.01); *G01N 2333/9513* (2013.01)

(58) Field of Classification Search
None
See application file for complete search history.

(56) References Cited

U.S. PATENT DOCUMENTS

| | | |
|---|---|---|
| 4,463,090 A | 7/1984 | Harris |
| 2002/0102577 A1 | 8/2002 | Raillard et al. |
| 2002/0127623 A1 | 9/2002 | Minshull et al. |
| 2008/0107660 A1 | 5/2008 | Self |
| 2010/0221212 A1 | 9/2010 | Stagliano et al. |
| 2011/0003312 A1 | 1/2011 | Berget |
| 2011/0143963 A1 | 6/2011 | Koide et al. |
| 2015/0226731 A1 | 8/2015 | Alexandrov et al. |

FOREIGN PATENT DOCUMENTS

| | | |
|---|---|---|
| WO | WO 02/10750 A2 | 2/2002 |
| WO | WO 2005/010198 A2 | 2/2005 |
| WO | WO 2005/083431 A2 | 9/2005 |
| WO | WO 2009/026338 A1 | 2/2009 |
| WO | WO 2009/062170 A1 | 5/2009 |
| WO | WO 2012/038950 A1 | 3/2012 |
| WO | WO 2014/040129 A1 | 5/2014 |

OTHER PUBLICATIONS

U.S. Appl. No. 60/986,475, Koide et al., filed Nov. 8, 2007.
Australian Patent Office, International Search Report in International Patent Application No. PCT/AU2014/000896 (Nov. 3, 2014).
International Bureau of WIPO, Written Opinion in International Patent Application No. PCT/AU2014/000896 (Mar. 24, 2016).
Binz et al. "Engineering novel binding proteins from nonimmunoglobulin domains," *Nature Biotechnology*, 23(10): 1257-1268 (Oct. 2005).
Huang et al., "Design of protein function leaps by directed domain interface evolution," *PNAS*, 105(18): 6578-6583 (May 6, 2008).
Huang et al., "Structural Basis for Exquisite Specificity of Affinity Clamps, Synthetic Binding Proteins Generated through Directed Domain-interface Evolution," *J. Mol. Biol.*, 392: 1221-1231 (2009).

(Continued)

*Primary Examiner* — Jacob Cheu
(74) *Attorney, Agent, or Firm* — Leydig, Voit & Mayer, Ltd.

(57) ABSTRACT

A biosensor comprises first and second molecular components and is capable of displaying protease activity in response to a binding event mediated by first and second binding partners of the biosensor. The first and second binding partners may bind each other directly or may both bind a target molecule. At least the first molecular component comprises an autoinhibited protease, whereby the binding event switches the protease frora an autoinhibited inactive state to a protease active state. The second molecular component may activate the protease of the first molecular component by binding a cross-binder which releases the autoinhibitor or by cleaving a linker which releases the autoinhibitor. The first and second molecular components may both have autoinhibited proteases which reciprocally activate each other.

45 Claims, 8 Drawing Sheets

(56) References Cited

OTHER PUBLICATIONS

Saghatelian et al., "DNA Detection and Signal Amplification via an Engineered Allosteric Enzyme," *J. Am. Chem. Soc.*, 125(2): 344-345 (2003).
Shekhawat et al., "Split-Protein Systems: Beyond Binary Protein-Protein Interactions," *Curr. Opin. Chem. Biol.*, 15(6): 789-797 (Dec. 2011).
Wehr et al., "Monitoring regulated protein-protein interactions using split TEV," *Nature Methods*, 3(12): 985-993 (Dec. 2006).
Zhuang et al. "Investigation of the binding specificity of Erbin-PDZ affinity clamp by molecular dynamics simulations," *Computational and Theoretical Chemistry*, 963: 448-452 (2011).
Carrington et al., *Journal of Virology*, 63(10): 4459-4463 (1989).
Guntas et al., *Chemistry & Biology*, 11: 1483-1487 (Nov. 2004).
Huang et al., *ACS Chem. Biol.*, 5(3): 273-277 (Mar. 19, 2010).
Ingallinella et al., *Biochemistry*, 37: 8906-8914 (1998).
O'Loughlin et al., *Comb. Chem. High Throughput Screen*, 9(4): 313-320 (May 2006).
Pallister et al., *Haematology $2^{nd}$ Edition*, Chapters 18.3-18.6: 336-347 (2011).
Saghatelian et al., *J. Am. Chem. Soc.*, 125: 344-345 (2003).
Shlyahovsky et al., *Angew. Chem. Int. Ed.*, 45: 4815-4819 (2006).
Stein et al., *PNAS*, 111(45): 15934-15939 (Nov. 11, 2014).
Stein et al., *Trends in Biotechnology*, 33(2): 101-110 (Feb. 2015).
Stein et al., "Synthetic Signal Sensing and Transduction Systems Based on Autoinhibited Proteases," *Poster presented at $6^{th}$ International Meeting on Synthetic Biology*, 9-11 Abstract (Jul. 2013).
Steinkuhler et al., *Biochemistry*, 37: 8899-8905 (1998).
Stratton et al., *Protein Science*, 20: 19-29 (2011).
Virel et al., *Anal. Chem.*, 84: 2380-2387 (2012).
Australian Patent Office, International Search Report in International Application No. PCT/AU2013/001039 (Nov. 22, 2013).
Australian Patent Office, Written Opinion in International Application No. PCT/AU2013/001039 (Nov. 22, 2013).
European Patent Office, Supplementary European Search Report in European Patent Application No. 13837496 (Mar. 8, 2016).
The International Bureau of WIPO, International Preliminary Report on Patentability in International Application No. PCT/AU2015/050669 (May 2, 2017).
United States Patent and Trademark Office, Office Action in U.S. Appl. No. 14/427,982 (Mar. 30, 2017).

A  Proteases transactivate reciprocally

B:   Scenario 2 AI-Protease P1 activates P2 unidirectionaly

C:   Scenario 3 Constitutively active Protease P1 activates P2 unidirectionaly

BIMOLECULAR PROTEASE-BASED BIOSENSOR

CROSS REFERENCE TO RELATED APPLICATIONS

This patent application is the U.S. national phase of International Patent Application No. PCT/AU2014/000896, filed Sep. 12, 2014, which claims the benefit of Australian Patent Application No. 2013903499, filed Sep. 12, 2013.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: One 38,460 Byte ASCII (Text) filed named "723502_ST25.txt," created Mar. 8, 2016.

TECHNICAL FIELD

THIS INVENTION relates to biosensors. More particularly, this invention relates to a biosensor comprising protease activity that is suitable for selective detection of one or more target molecules. The biosensor may be used to detect molecules in biological, clinical, environmental and industrial samples. The biosensor may also relate to the field of synthetic biology such as for constructing artificial cellular signalling networks.

BACKGROUND

Detection of target molecules or analytes is a key to understanding and controlling complex biological processes such as organismal growth, metabolism, differentiation, cell- and life cycle progression, disease or death. Key requirements of analyte detection are specificity and sensitivity, particularly when the target molecule or analyte is in a limiting amount or concentration in a biological sample.

Typically, specificity is provided by monoclonal antibodies which specifically bind the analyte. Sensitivity is typically provided by a label bound to the specific antibody, or to a secondary antibody which assists detection of relatively low levels of analyte. This type of diagnostic approach has become well known and widely used in the enzyme-linked immunosorbent sandwich assay (ELISA) format. In some cases, enzyme amplification can even further improve sensitivity such as by using a product of a proenzyme cleavage reaction catalyzing the same reaction. Some examples of such "autocatalytic" enzymes are trypsinogen, pepsinogen, or the blood coagulation factor XII. However, in relation to specificity antibodies are relatively expensive and can be difficult to produce with sufficient specificity for some analytes. Polyclonal antibodies also suffer from the same shortcomings and are even more difficult to produce and purify on a large scale.

Current methods to detect specific target molecules and analytes for either prognostic or diagnostic purposes suffer from a number of limitations which significantly restrict their widespread application in clinical, peri-operative and point-of-care settings. Most importantly, the vast majority of diagnostic assays require a significant level of technical expertise and a panel of expensive and specific reagents (most notably monoclonal antibodies) along with elaborate biomedical infrastructures which are rarely available outside specialized laboratory environments. For instance, ELISAs—the gold standard for detecting specific analytes in complex biological samples—rely on the selective capture of a target analyte on a solid surface which in turn is detected with a second affinity reagent that is specific for the target analyte. ELISAs also feature extensive incubation and washing steps which are generally time consuming and difficult to standardize as the number of successive steps frequently introduces significant variation across different procedures, operators and laboratories making quantitative comparisons difficult.

SUMMARY

The present invention addresses a need to develop a quantitative, relatively inexpensive and easily produced molecular biosensor that readily detects the presence or the activity of target molecules rapidly and sensitively. It is also an objective to produce a molecular biosensor that has broad applicability in cellular engineering, molecular diagnostics, drug screening, biomarker detection and other applications that require detection of binding events.

In one broad form the invention relates to a biosensor comprising a first molecular component and a second molecular component, at least one of which components comprises a protease amino acid sequence which is switchable from a protease inactive to a protease active state, or from a protease active to an inactive state, in response to a binding event between the first molecular component and the second molecular component.

In a preferred broad form, the invention relates to a biosensor comprising a first molecular component having a first binding partner and a second molecular component having a second binding partner, at least one of which components comprises a protease amino acid sequence which is switchable from a protease inactive to a protease active state, or from a protease active to an inactive state, in response to a binding event comprising the first binding partner and the second binding partner binding a target molecule.

In a preferred form, the first molecular component comprises a protease amino acid sequence which is switchable from a protease inactive to a protease active state.

Particular aspects and embodiments of the invention are set forth hereinafter.

In a first aspect, the biosensor comprises first and second molecular components wherein: the first molecular component comprises: a first binding partner, a protease amino acid sequence and an inhibitor of the protease activity of said protease; and the second molecular component comprises: a second binding partner and a subcomponent capable of facilitating: (i) at least partial release of inhibition of the protease of the first molecular component by the inhibitor to switch the protease of the first molecular component from a protease inactive to a protease active state; or (ii) at least partial inhibition of the protease of the first molecular component by the inhibitor to switch the protease of the first molecular component from a protease active to a protease inactive state; upon a binding interaction between the first and second binding partners.

Preferably, the biosensor comprises first and second molecular components wherein: the first molecular component comprises: a first binding partner a protease amino acid sequence and an inhibitor of the protease activity of said protease; and the second molecular component comprises: a second binding partner and a subcomponent capable of facilitating at least partial release of inhibition of the protease of the first molecular component by the inhibitor to switch the protease of the first molecular component from a protease inactive to a protease active state upon a binding interaction between the first and second binding partners.

In some embodiments, the first binding partner and the second binding partner may be capable of binding, coupling, interacting or forming a complex with a target molecule to thereby co-localize the first molecular component and the second molecular component to facilitate at least partial release of inhibition of the protease of the first molecular component.

In other embodiments, the first binding partner and the second binding partner may be capable of directly binding, coupling, interacting or forming a complex to thereby co-localize the first molecular component and the second molecular component to facilitate at least partial release of inhibition of the protease of the first molecular component.

Suitably, the first binding partner and the second binding partner are different molecules (e.g. proteins, nucleic acids, sugars, lipids or combinations of these although without limitation thereto) or are different portions, parts, segments, moieties, domains, regions, sub-sequences or fragments of the same molecule.

In one broad embodiment, the subcomponent of the second molecular component comprises an amino acid of another protease. Preferably, according to this broad embodiment, the first molecular component further comprises at least one protease cleavage site cleavable by said another protease. Suitably, cleavage of the protease cleavage site by the protease of the second molecular component releases the protease-inhibitory effect of the inhibitor to thereby switch the first molecular component of the biosensor from a protease inactive to a protease active state. In one embodiment, said another protease is constitutively active. In another embodiment, the second molecular component comprises an inhibitor of said another protease. In a further form of this embodiment, the second molecular component further comprises at least one protease cleavage site cleavable by the protease of the first molecular component and an inhibitor of said another protease, whereby cleavage of the protease cleavage site of the second molecular component by the protease of the first molecular component at least partly releases inhibition of said another protease by the inhibitor to thereby switch the second molecular component of the biosensor from a protease inactive to a protease active state.

In an alternative broad embodiment, the subcomponent of the second molecular component comprises an amino acid sequence of a protein or protein fragment that is not of a protease. In one form of this embodiment, the first molecular component comprises a cross-binder that is capable of binding said amino acid sequence that is not of a protease. Suitably, the cross-binder is linked or connected to the inhibitor of the protease of the first molecular component. Suitably, said amino acid sequence that is not of a protease is capable of binding or being bound by the cross-binder. In use, binding between the first binding partner and the second binding partner and, optionally a target molecule, co-localizes the first molecular component and the second molecular component thereby facilitating binding of the cross-binder by said amino acid sequence that is not of a protease to thereby at least partly release inhibition of the protease of the first molecular component by the inhibitor and switch the protease of the first molecular component from a protease inactive to a protease active state. In particular embodiments, said amino acid sequence that is not of a protease may be of calmodulin or of an affinity clamp such as a PDZ fusion with an FN3 domain, as will be described in more detail hereinafter.

In one embodiment, the protease of the first and/or second molecular components is an endopeptidase. Preferably, the endopeptidase is a cysteine protease.

In another embodiment, the protease of the first and/or second molecular components is derivable or obtainable from a virus.

In certain embodiments the virus is a Potyvirus such as, tobacco vein mottling virus (TVMV), tobacco etch virus (TEV) or sugarcane mosaic virus (SMV) or a Flavivirus such as Hepatitis C Virus (HCV).

Preferably, the protease is an NIa protease.

In some embodiments, the inhibitor is a peptide. A preferred inhibitor peptide is an autoinhibitory peptide.

In particular embodiments, the autoinhibitor peptide is an autoinhibitor of an NIa protease of a Potyvirus.

In a preferred form, the first molecular component and the second molecular component are separate, recombinant fusion proteins. Amino acid sequences of particular embodiments of the first molecular component, second molecular component and constituent subcomponents, proteases, protease inhibitors, cross-binders and other portions thereof are set forth in SEQ ID NOS:1-18. Also provided are fragments, derivatives and variants of the amino acid sequences set forth in SEQ ID NOS:1-18.

Another aspect of the invention provides a composition or kit comprising the biosensor of the aforementioned aspect and a substrate.

In one embodiment, the substrate comprises an amino acid sequence cleavable by the biosensor protease of the biosensor.

In another embodiment, the composition or kit further comprises an amplifier molecule.

Suitably, the amplifier molecule is capable of amplifying a signal elicited by the biosensor in a protease active state.

Suitably, the amplifier molecule comprises: (i) an amino acid sequence of a protease that is different to the protease of the biosensor; (ii) an inhibitor of the protease of (i); and (iii) a linker amino acid sequence which comprises a cleavage site for the protease of the biosensor.

In one particular embodiment, the biosensor may be linked or coupled to the amplifier molecule. For example, the biosensor and amplifier molecule may comprise respective interacting domains (i.e an amplifier interacting domain and a biosensor interacting domain) that facilitate releasable linking or coupling of the biosensor and amplifier molecules.

Preferably, the composition or kit further comprises a deactivating molecule.

Suitably, the deactivating molecule comprises: (i) an amino acid sequence of a protease that is different to the protease of the biosensor and that is different to the protease of the amplification molecule; (ii) an inhibitor of the protease of (i); and (iii) a linker amino acid sequence which comprises a cleavage site for the protease of the amplification molecule.

Suitably, according to this embodiment, the substrate comprises an amino acid sequence cleavable by the protease of the amplification molecule.

The protease and the protease inhibitor may be any of the proteases and inhibitors disclosed herein in relation to the biosensor protease. Preferably, the protease of the amplifier molecule is different to the protease(s) of the biosensor.

Preferably, the protease of the deactivating molecule is different to the proteases of the biosensor and the amplifier molecule.

The composition or kit may comprise one or a plurality of different biosensors disclosed herein capable of detecting one or a plurality of different target molecules.

In some embodiments, the composition may be in form of a single, mixed reagent that comprises one or more of the biosensors, the amplifier molecule, the deactivating molecule and the substrate.

In some embodiments, the kit may separately provide or more of the biosensor, the amplifier molecule, the deactivating molecule and the substrate as individual components.

A further aspect of the invention provides a method of detecting a binding interaction between the first and second molecular components of the biosensor of the aforementioned aspect, said method including the step of contacting the composition of the aforementioned aspect with a sample to thereby determine the presence or absence of the target molecule in the sample.

Another further aspect of the invention provides a method of detecting a target molecule, said method including the step of contacting the biosensor of the aforementioned aspect with a sample to thereby determine the presence or absence of the target molecule in the sample.

A still further aspect of the invention provides a method of diagnosis of a disease or condition in an organism, said method including the step of contacting the of the biosensor of the aforementioned aspect with a biological sample obtained from the organism to thereby determine the presence or absence of a target molecule in the biological sample, determination of the presence or absence of the target molecule facilitating diagnosis of the disease or condition.

The organism may include plants and animals inclusive of fish, avians and mammals such as humans.

A still yet further aspect of the invention provides a detection device that comprises a cell or chamber that comprises the biosensor of the first aspect.

Suitably, a sample may be introduced into the cell or chamber to thereby facilitate detection of a target molecule.

In certain embodiments, the detection device is capable of providing an electrochemical, acoustic and/or optical signal that indicates the presence of the target molecule.

The detection device may further provide a disease diagnosis from a diagnostic target result by comprising:
  a processor; and
  a memory coupled to the processor, the memory including computer readable program code components that, when executed by the processor, perform a set of functions including:
  analysing a diagnostic test result and providing a diagnosis of the disease or condition.

The detection device may further provide for communicating a diagnostic test result by comprising:
  a processor; and
  a memory coupled to the processor, the memory including computer readable program code components that, when executed by the processor, perform a set of functions including:
  transmitting a diagnostic result to a receiving device; and
  optionally receiving a diagnosis of the disease or condition from the or another receiving device.

A related aspect of the invention provides an isolated nucleic acid encoding the first molecular component and/or the second molecular component of the biosensor of the aforementioned aspect.

Another related aspect of the invention provides a genetic construct comprising the isolated nucleic acid of the aforementioned aspect.

A further related aspect of the invention provides a host cell comprising the genetic construct of the aforementioned aspect.

It will be appreciated that the indefinite articles "a" and "an" are not to be read as singular indefinite articles or as otherwise excluding more than one or more than a single subject to which the indefinite article refers. For example, "a" molecule includes one molecule, one or more molecules or a plurality of molecules.

As used herein, unless the context requires otherwise, the words "comprise", "comprises" and "comprising" will be understood to mean the inclusion of a stated integer or group of integers but not the exclusion of any other integer or group of integers.

Figure 1:
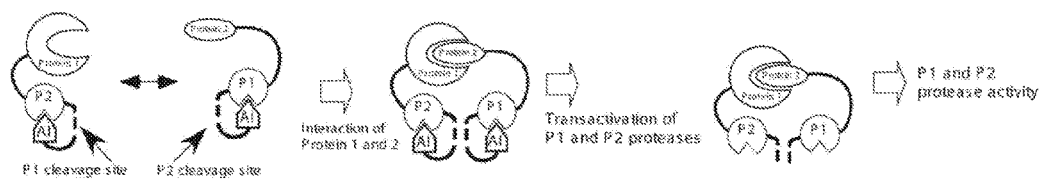
FIG. 1: A proteolytic transactivator interaction switch comprising first and second molecular components. A: First (P1) and second (P2) proteases transactivate reciprocally. B: AI-second protease (P1) activates first protease unidirectionaly. C: Constitutively active second protease (P2) activates first protease (P1) unidirectionally.
Figure 1:
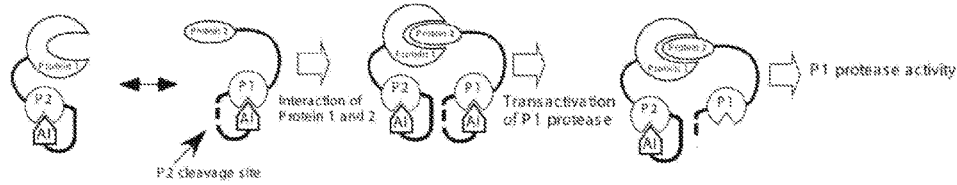
Figure 1:
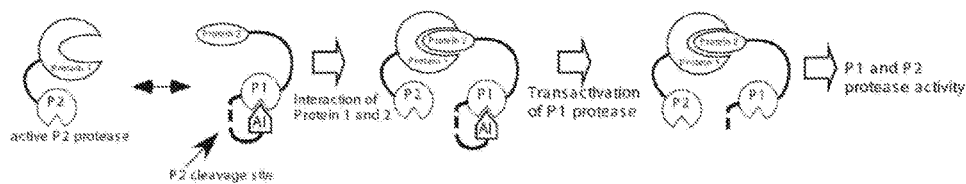
Figure 2:
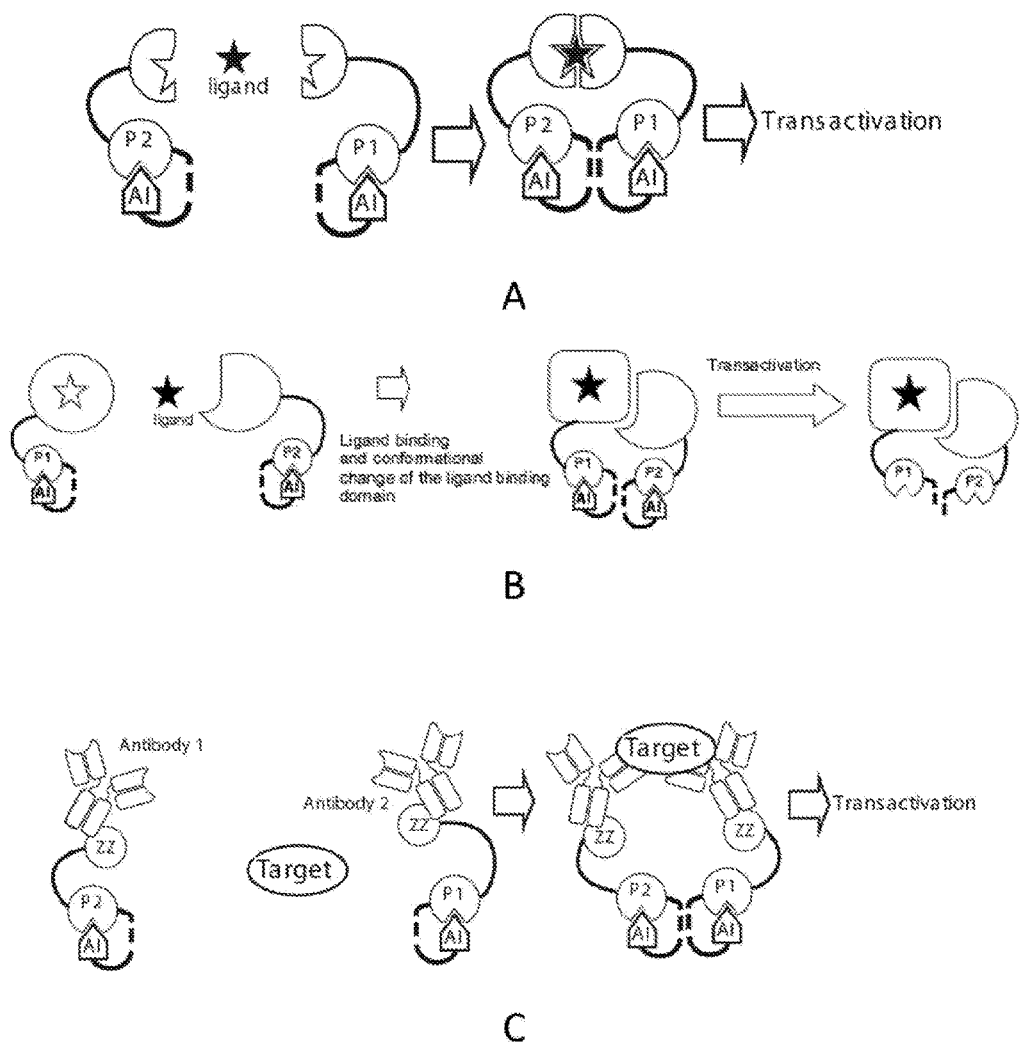
FIG. 2: A proteolytic transactivator interaction switch comprising first and second molecular components. (A) The concept of transactivator protease switch based on two orthogonal autoinhibited proteases activated by ligand-mediated protein:protein interactions of first and second binding partners. (B) A two-component biosensor protease transactivator system based on interactions between first and second binding partners mediated by a target molecule ligand binding to one of the components. (C) A two-component biosensor protease transactivator based system for detecting biomarker target molecules bound by first and second binding partner antibodies. The first and second proteases are fused to ZZ antibody-binding domains.

Schematic representation of the sensor (B) activation of 1 µM of the TVMV-AI-Affinity clamp binding peptide sensor by affinity clamp, a combination of affinity clam and affinity clam binding peptide or thrombin. The full activation is achieved by exposing the biosensor to thrombin that cleaves it between TVMV and AI. (C) titration of XXnM of the TVMV-AI-Affinity clamp binding peptide sensor with increasing concentrations of affinity clamp. (D) fit of the initial rates obtained (C) to a quadratic equation to obtain the apparent Kd value for sensor interaction with the affinity clamp.

FIG. 6: (A) A rapamycin-binding two-component biosensor comprising: a first molecular component comprising TVMV protease fused to a cross-binder of ePDZ, an autoinhibitor peptide and rapamycin-binding FRB; and a second molecular component comprising ePDZ fused to FKBP12 and rapamycin-binding FKBP12; (B) graph showing activation of TVMV protease activity of FRB-TVMV-AI-affinity clamp peptide addition of affinity clamp or Affinity clamp-FRB or Affinity clamp-FRB and rapamycin. Thrombin cleaves the protein between TVMV and AI. Experiments were performed as described in FIG. 4

FIG. 7: Transactivating proteolytic tow component receptors. (A) Principle design of autoinhibited protease-based proximity sensors. A TVMV-inducible mutant of HCV was fused to FRB and a thrombin-inducible mutant of TVMV was fused to FKBP12. In the presence of rapamycin, TVMV co-localizes with HCV resulting in rapid cleavage of the latter. (B, C) Time resolved traces of protease activities of HCV activity of the sensors in the absence (red) or presence (blue) of rapamycin. Note that background activation is significantly reduced in the presence of the AI-domain (D, E). Titration of rapamycin to the two component sensor induces HCV activation at sub pM concentrations. (F). Quantification of Kds for rapamycin for uninhibited TVMV at different ligand concentrations. Proteases were assayed with 5 μM quenched fluorescent substrate peptide.

FIG. 8: Dual specificity two-component biosensor. (A) The first molecular component is a fusion protein that comprises an SH3 domain binding partner, HCV protease, an intermediate linker comprising a TVMV protease cleavage site and an autoinhibitor of the HCV protease. The second molecular component is a fusion protein that comprises a PDZ domain binding partner, TVMV protease, an intermediate linker comprising a HCV protease cleavage site an autoinhibitor of the TVMV protease. The target molecule comprises EGFP N-terminally fused to a ligand for an SH3 domain binding partner and C-terminally fused to a ligand for a PDZ domain binding partner. (B) Graph showing activation of HCV protease activity in the presence of 200 nM of each component and indicated concentrations of SH3 binding peptide(SH3bp)-EGFP-PDZ binding peptide (PDZbp).

DETAILED DESCRIPTION

The present invention provides a biosensor comprising first and second molecular components which is capable of displaying protease activity in response to a binding event. Suitably the first and second molecular components respectively comprise first and second binding partners. The first and second binding partners may bind each other directly or may both bind a target molecule. This binding event brings the first and second molecular components into the proximity of each other. Suitably, the first molecular component comprises an autoinhibited protease, whereby the binding event mediated by the first and second binding partners switches the protease from an autoinhibited "inactive" state to a protease "active" state. In alternative embodiments, the protease is initially in an "active" state which is then inactivated following the binding event due to the inhibitor suppressing or inhibiting the protease activity of the biosensor.

In one embodiment, a cross-binder amino acid sequence connects the protease amino acid sequence and the inhibitor in a manner which subsequently allows the cross-binder to bind the subcomponent of the second molecular component once the binding event brings the first and second molecular components into the proximity of each other. Preferably, binding of the second molecular component proteolytically removes or allosterically releases the inhibitor from inhibiting the protease, thereby activating the protease. In one particular form, the subcomponent of the second molecular protease may comprise a non-protease molecule such as an affinity clamp or calmodulin amino acid sequence and the cross-binder is capable of reversibly binding the affinity clamp or calmodulin, respectively. In another embodiment, the first molecular component comprises a protease amino acid sequence and the subcomponent of the second molecular component comprises another protease amino acid sequence. The first molecular component and/or the second molecular component may further comprise protease inhibitors and cleavage sites for one or the other proteases. Proteolytic cleavage of one or the other cleavage sites releases inhibition or suppression of protease activity. In this broad embodiment, the binding event may result in unidirectional activation of the first molecular component protease or the second molecular component protease, or bidirectional activation of the first molecular component protease or the second molecular component protease.

The protease activated biosensor molecule of either embodiment may proteolytically cleave a labeled substrate to facilitate generation of a detectable signal. In further embodiments, the signal produced by the protease active biosensor molecule may be amplified by way of an amplifier molecule which will be described in more detail hereinafter.

The biosensor disclosed herein may have particular efficacy in molecular diagnostics or analytics wherein the target molecule is an analyte or other molecule of diagnostic value or other importance. However, another application of the biosensor disclosed herein may be in synthetic biology applications for constructing multi-component artificial cellular signalling networks regulating cellular processes, the detection of protein:protein, protein:small molecule interactions, antibody-mediated detection of antigens and biomarkers as well as the construction of in vivo screening and selection systems comparable to two hybrid systems.

For the purposes of this invention, by "isolated" is meant material (such as a molecule) that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated proteins and nucleic acids may be in native, chemical synthetic or recombinant form.

By "protein" is meant an amino acid polymer. The amino acids may be natural or non-natural amino acids, D- or L-amino acids as are well understood in the art.

A "peptide" is a protein having less than fifty (50) amino acids.

A "polypeptide" is a protein having fifty (50) or more amino acids.

A "protease" is any protein which displays, or is capable of displaying, an ability to hydrolyse or otherwise cleave a peptide bond. Like terms include "proteinase" and "peptidase". Proteases include serine proteases, cysteine proteases, metalloproteases, threonine proteases, aspartate proteases, glutamic acid proteases, acid proteases, neutral proteases, alkaline proteases, exoproteases, aminopeptidases and endopeptidases although without limitation thereto. Proteases may be purified or synthetic (e.g. recombinant synthetic) forms of naturally-occurring proteases or may be engineered or modified proteases which comprise one or more fragments or domains of naturally-occurring proteases which, optionally, have been further modified to possess one or more desired characteristics, activities or properties.

Proteases are found throughout nature, including viruses, bacteria, yeasts, plants, invertebrate animals and vertebrates inclusive of mammals and humans, although without limitation thereto. Accordingly, proteases are involved in a variety of different physiological processes including digestion of food proteins, blood-clotting cascades, the complement system, apoptosis pathways, the invertebrate prophenoloxidase-activating cascade, bacterial exotoxins and processing of viral proteins, although without limitation thereto.

An aspect of the invention provides the biosensor comprises first and second molecular components wherein: the first molecular component comprises: a first binding partner, a protease amino acid sequence and an inhibitor of the protease activity of said protease; and the second molecular component comprises: a second binding partner and a subcomponent capable of facilitating: (i) at least partial release of inhibition of the protease of the first molecular component by the inhibitor to switch the protease of the first molecular component from a protease inactive to a protease active state; or (ii) at least partial inhibition of the protease of the first molecular component by the inhibitor to switch the protease of the first molecular component from a protease active to a protease inactive state; upon a binding interaction between the first and second binding partners.

While the terms "first" and "second" are used in the context of respective, separate or discrete molecular components and/or first and second binding partners of the biosensor, it will be appreciated that these do not relate to any particular non-arbitrary ordering or designation that cannot be reversed. Accordingly, the structure and functional properties of the first molecular component and the second molecular component disclosed herein could be those of a second molecular component and a first molecular component, respectively. Similarly, the structure and functional properties of the first binding partner and the second binding partner disclosed herein could be those of a second binding partner and a first binding partner, respectively. It will also be appreciated that the biosensor may further comprise one or more other, non-stated molecular components.

In this context, a "molecular component" is a discrete molecule that forms a separate part, portion or component of the biosensor. In typical embodiments, each molecular component is, or comprises, a single, contiguous amino acid sequence (i.e a fusion protein). While it will be apparent that in many embodiments the first and second molecular components may non-covalently bind, couple, interact or associate in the context of a "binding event" mediated by the first and second binding partners, they remain discrete molecules that form the biosensor.

The present invention broadly provides a first molecular component of the biosensor that comprises a protease amino acid sequence, wherein the protease amino acid sequence is capable of displaying protease activity.

The protease amino acid sequence may be an entire amino acid sequence of a protease or may be an amino acid sequence of a proteolytically-active fragment or sub-sequence of a protease.

In one preferred embodiment, the protease is an endopeptidase.

Preferably, the endopeptidase is a cysteine protease or serine protease. A particular example of a cysteine protease is NIa protease of Potyviruses. A particular example of a serine protease is an NS3 protease of a Flavivirus such as HCV.

In another preferred embodiment, the protease is a naturally-occurring protease.

A preferred class of proteases are derived from, or encoded by, a viral genome. Typically, such proteases are dependent on expression and proteolytic processing of a polyprotein and/or other events required as part of the life cycle of viruses such as Picornavirales, Nidovirales, Herpesvirales, Retroviruses and Adenoviruses, although without limitation thereto. Particular examples of proteases include: Potyviridae proteases such as the NIa protease of tobacco etch virus (TEV), tobacco vein mottling virus (TVMV), sugarcane mosaic virus (SMV) etc; Flaviviridae proteases such as the NS3 protease of hepatitis C virus (HCV); Picornaviridae proteases such as the 3C protease of EV71, Norovirus etc, the 2A protease of human rhinovirus, coxsackievirus B4 etc and the leader protease of foot and mouth disease virus (FMDV) etc; Coronaviridae proteases such as the 3C-like protease of SARS-CoV, IBV-CoV and Herpesvirus proteases such as HSV-1, HSV-2, HCMV and MCMV proteases etc, although without limitation thereto.

Preferably, the viral genome is of a plant virus.

More preferably, the plant virus is a Potyvirus.

In a particularly preferred embodiment, the protease is an auto-inhibited Potyvirus protease such as the NIa protease of TEV, TVMV or SMV.

In an alternative embodiment the protease is an autoinhibited NS3 protease of HCV.

The native function of NIa proteases from Potyviridae is to process the viral polyprotein proteome. Auto-inhibition is mediated by peptides that bind the active site of NIa proteases and inhibit their activity. Such inhibitors are typically derived from Site F which separates the NIb RNA polymerase from the viral coat protein, and is considered the most efficient substrate for NIa proteases.

It will be appreciated that the biosensor of the invention is capable of displaying protease activity which can be at least partly inhibited by an inhibitor of the protease activity.

Accordingly, in this context, "switchable from a protease inactive to a protease active state" may include an increase in protease activity from a less or partly active state to a more or fully active state or from a substantially inactive or inhibited state to a substantially active or substantially uninhibited state. Alternatively in this context, "switchable from a protease active to a protease inactive state" may include a decrease in protease activity from a more active state or fully active state to less active state or a substantially inactive or inhibited state.

The inhibitor may be any molecule which at least partly, or substantially or totally suppresses or inhibits the protease activity of the amino acid sequence of the protease. The inhibitor may be a non-specific inhibitor by virtue of having inhibitory activity towards a plurality of different proteases or types of protease, or may be a specific inhibitor by virtue of substantially inhibiting only a single protease.

The inhibitor may be a protein (inclusive of peptides) or a non-protein organic molecule such as a small organic molecule, a lipid, a carbohydrate or a nucleic acid, although without limitation thereto.

Non-limiting examples of protease inhibitors that are proteins include viral autoinhibitory peptides, aprotinin, leupeptin, metallocarboxypeptidase A inhibitor, α2 macroglobulin, pepstatin and serpins such as alpha 1-antitrypsin, C1-inhibitor, antithrombin, alpha 1-antichymotrypsin, plasminogen activator inhibitor-1 and neuroserpin, although without limitation thereto. Inhibitors can comprise specific antibody or antibody fragments displaying inhibitory activity, protein domains or peptides displaying specific binding to the protease and exerting competitive, steric or allosteric inhibition, DNA, PNA or RNA aptamers capable of binding to the protease and exerting competitive, steric or allosteric inhibition.

Non-limiting examples of protease inhibitors that are organic molecules include phenylmethanesulfonyl fluoride, tosyl lysine chloromethylketone, tosyl phenylalanyl chloromethyl ketone, bestatin and nitrophenol-p-guanidino benzoate, phosphoramidite and protease inhibitors developed as antiviral agents, such as for treatment of HIV or hepatitis C infection. Non-limiting examples of antiviral protease inhibitors include ritonivir, saquinavir, indinavir, nelfinavir, tipranavir, amprenavir and daurnavir, although without limitation thereto.

Suitably, the protease inhibitor is a reversible protease inhibitor.

The inhibitor may be an active site inhibitor or an allosteric inhibitor of the protease.

Preferably, the protease inhibitor is an autoinhibitory peptide. Suitably, the autoinhibitory peptide comprises an amino acid sequence which binds the active site of a protease without being cleaved by the protease. Preferably, the autoinhibitory peptide competitively at least partly inhibits binding and cleavage of one or more protease substrates by the protease. In one embodiment, the autoinhibitory peptide is a specific inhibitor of an endopeptidase such as a cysteine protease. In a preferred embodiment, the autoinhibitory peptide is a specific inhibitor of a protease, preferably a cysteine protease, encoded by a viral genome.

More preferably, the autoinhibitory peptide is an inhibitor of a protease encoded by a Potyviral genome.

One particular embodiment of an autoinhibitory peptide is a specific inhibitor of a Potyvirus NIa protease, preferably encoded by a TEV, TVMV or SMV genome. Peptides that bind the active site of NIa proteases and inhibit their activity are generally derived from Site F which refers to a peptide sequence which separates the NIb RNA polymerase from the viral coat protein, and is considered the most efficient substrate for NIa proteases.

The autoinhibitory peptide may comprise an amino acid sequence that corresponds to at least a fragment of a substrate of the protease, but not an amino acid sequence of a protease cleavage site. In this regard, the autoinhibitory peptide may comprise an amino acid sequence that corresponds to that of a cleavage product or comprise an amino acid sequence of a protease cleavage site modified or engineered to resist cleavage by the protease.

In some embodiments, to improve binding of the autoinhibitory peptide to the protease, and thus achieve improved autoinhibition, one or more amino acid sequence mutations may be introduced into the amino acid sequence of the protease and/or the autoinhibitor. As will be described in more detail hereinafter in the Examples in embodiments relating to NIa protease of TVMV, modification of residues in the 'RETVRFQSDT' (SEQ ID NO: 19) of the site F autoinhibitory peptide may improve auto-inhibition while minimizing or eliminating cleavage by TVMV protease.

Binding of the autoinhibitory peptide can also be improved by improving the linker region connecting the autoinhibitory (AI) domain to the NIa protease, such as by truncating the C-terminus of TVMV and increasing the effective concentration of the AI domain near the active site.

In other embodiments, autoinhibition can be improved by introducing beneficial steric constraints either through specific dimerization modules located at the N- and C-terminus of the protease biosensor or by circular permutation. Circularly permutated protease biosensors may feature two linker sites which can incorporate recognition sites for two different target proteases.

Persons skilled in the art will appreciate that the modifications described above in relation to NIa proteases and autoinhibitory peptides may be applied in principle to other proteases and/or autoinhibitory peptides suitable for use in biosensors.

For example, in a manner analogous to NIa proteases, artificially autoinhibited signal transducers based on HCV can be created by joining the peptide-based active site binder DELILCPLDL (SEQ ID NO:20) to its C-terminus via a linker comprising a TVMV cleavage site.

As will be understood from the foregoing, the first molecular component of the biosensor may be a single, unitary or contiguous protein molecule (e.g a fusion protein) comprising a protease amino acid sequence; a first binding partner acid sequence; and an amino acid sequence of an inhibitor of the protease activity of said protease amino acid sequence; wherein the biosensor is switchable between a protease active and a protease inactive state, or from a protease inactive to a protease active state when said said first and second binding partners bind directly or bind said target molecule.

Suitably, the protease amino acid sequence and the first binding partner amino acid sequence are contiguous, or optionally, connected by a linker amino acid or amino acid sequence. The first binding partner amino acid sequence may be contiguous or linked to the N- or C-terminal amino acid of the protease amino acid sequence.

In embodiments where the inhibitor of protease activity comprises an amino acid sequence (i.e. is a protein or peptide), this is preferably fused or connected to the protease amino acid sequence by a linker amino acid sequence. In some embodiments, the linker amino acid sequence is, or comprises a cross-binder, as will be described in more detail hereinafter. In other embodiments, the linker amino acid sequence is, or comprises a cleavage site for another protease, as will be described in more detail hereinafter.

Other particular embodiments of the first molecular component may include circularly permutated protease constructs and split protease constructs such as described in WO2014/040129, although without limitation thereto.

In embodiments where the inhibitor of protease activity does not comprise an amino acid sequence (e.g. is a small organic molecule, nucleic acid etc), the inhibitor is suitably covalently coupled directly or indirectly to the amino acid sequence of the first molecular component. Covalent coupling may be achieved by standard chemical methods depending on the chemical structure of the inhibitor utilized.

In a preferred broad form, the biosensor comprises a second molecular component comprising a second binding partner and a subcomponent capable of facilitating at least partial release of inhibition of the protease of the first molecular component by the inhibitor to switch the protease of the first molecular component from a protease inactive to a protease active state upon a binding interaction between the first and second binding partners. In an alternative broad form, the biosensor comprises a second molecular component comprising a second binding partner and a subcomponent capable of facilitating inhibition of the protease of the first molecular component by the inhibitor to switch the protease of the first molecular component from a protease active to a protease inactive state upon a binding interaction between the first and second binding partners.

The binding interaction between the first binding partner of the first molecular component and the second binding partner of the second molecular component suitably facilitates co-localization of the first and second molecular components. In one general embodiment, this facilitates at least partial release of inhibition of the protease of the first molecular component by the inhibitor to switch the protease of the first molecular component from a protease inactive to a protease active state.

The first binding partner and/or the second binding partner may be proteins, nucleic acids (e.g DNA or RNA), sugars, oligosaccharides, polysaccharides or other carbohydrates, lipids or any combinations of these such as glycoproteins, PNA constructs etc. By way of example only, the first binding partner and/or second binding partner may be, or comprise: (i) an amino acid sequence of a ligand binding domain of a receptor responsive to binding of a target molecule such as a cognate growth factor, cytokine, a hormone (e.g. insulin), neurotransmitters etc; (ii) an amino acid sequence of an ion or metabolite transporter capable of, or responsive to, binding of a target molecule such as an ion or metabolite (e.g a $Ca^{2+}$-binding protein such as calmodulin or a glucose transporter); (iii) a zinc finger amino acid sequence responsive to zinc-dependent binding a DNA target molecule; (iv) a helix-loop-helix amino acid sequence responsive to binding a DNA target molecule; (v) a pleckstrin homology domain amino acid sequence responsive to binding of a phosphoinositide target molecule; (vi) an amino acid sequence of a Src homology 2- or Src homology 3-domain responsive to a signaling protein; (vii) an amino acid sequence of an antigen responsive to binding of an antibody target molecule; or (viii) an amino acid sequence of a protein kinase or phosphatase responsive to binding of a phosphorylatable or phosphorylated target molecule; (ix) ubiquitin-binding domains; (x) proteins or protein domains that bind small molecules, drugs or antibiotics such as rapamycin-binding FKBP and FRB domains; (xi) single- or double-stranded DNA, RNA or PNA constructs that bind nucleic acid target molecules, such as where the DNA or RNA are coupled or cross-linked to an amino acid sequence or other protein-nucleic acid interaction; and/or (xii) an affinity clamp such as a PDZ-FH3 domain fusion; inclusive of modified or engineered versions thereof, although without limitation thereto.

It will also be appreciated that the first binding partner and/or the second binding partner may be modified or chemically derivatized such as with binding agents such as biotin, avidin, epitope tags, lectins, carbohydrates, lipids although without Imitation thereto.

In some embodiments the first binding partner and the second binding partner may directly bind, interact or form a complex. The first binding partner and the second binding partner may comprise molecules that can directly bind or interact. Accordingly, the direct binding interaction between the target molecule and the first binding partner of the first molecular component and the second binding partner of the second molecular component suitably facilitates co-localization of the first and second molecular components. Non-limiting examples are shown schematically in FIG. 1.

In other embodiments, the first binding partner and the second binding partner are capable of binding, interacting or forming a complex with a target molecule. Typically, the first binding partner and the second binding partner are capable of binding, interacting or forming a complex with the same target molecule. By way of example, the first binding partner and the second binding partner may comprise amino acid sequences of respective proteins or protein domains or fragments that are capable of binding different portions or moieties of the same target molecule. In some embodiments, the first binding partner and the second binding partner are capable of co-operatively binding the target molecule. Accordingly, the binding interaction between the target molecule and the first binding partner of the first molecular component and the second binding partner of the second molecular component suitably facilitates co-localization of the first and second molecular components. Non-limiting examples are shown schematically in FIGS. 2-8. It will be appreciated that as shown in FIG. 8, the "same" target molecule can have respective, different moieties, subunits, domains, ligands or epitopes that can be bound by the respective first and second binding partners to thereby co-localize and activate protease activity. Biosensors of this general type may be referred to as "dual specificity" biosensors.

In this regard, the target molecule may be any ligand, analyte, epitope, domain, fragment, subunit, moiety or combination thereof, such as a protein inclusive of antibodies and antibody fragments, antigens, phosphoproteins, glycoproteins, lipoproteins and glycoproteins, lipid, phospholipids, carbohydrates inclusive of simple sugars, disaccharides and polysaccharides, nucleic acids, nucleoprotein or any other molecule or analyte. These include drugs and other pharmaceuticals including antibiotics, chemotherapeutic agents and lead compounds in drug design and screening, molecules and analytes typically found in biological samples such as biomarkers, tumour and other antigens, receptors, DNA-binding proteins inclusive of transcription factors, hormones, neurotransmitters, growth factors, cytokines, receptors, metabolic enzymes, signaling molecules, nucleic acids such as DNA and RNA, membrane lipids and other cellular components, pathogen-derived molecules inclusive of viral, bacterial, protozoan, fungal and worm proteins, lipids, carbohydrates and nucleic acids, although without limitation thereto. As previously, described, it will be appreciated that as shown in FIG. 8, the "same" target molecule can have respective, different moieties, subunits, domains, ligands or epitopes that can be bound by the respective first and second binding partners.

In one embodiment, the first and/or second binding partners comprise an amino acid sequence of at least a fragment of any protein or protein fragment or domain that can bind or interact directly, or bind to a target molecule. The binding partner may be, or comprise a protein such as a peptide, antibody, antibody fragment or any other protein scaffold that can be suitably engineered to create or comprise a binding portion, domain or region (e.g. reviewed in Binz et al., 2005 Nature Biotechnology, 23, 1257-68.) which binds a target molecule.

In one particular embodiment, the first binding partner and/or the second binding partner is or comprises an amino acid sequence of an affinity clamp. The affinity clamp preferably comprises a recognition domain and, optionally, an enhancer domain. The recognition domain is typically capable of binding one or more target molecules, such as described in (i)-(ix) above. Recognition domains may include, but are not limited to, domains involved in phoshotyrosine binding (e.g. SH2, PTB), phospho-serine binding (e.g. UIM, GAT, CUE, BTB/POZ, VHS, UBA, RING, HECT, WW, 14-3-3, Polo-box), phospho-threonine binding (e.g. FHA, WW, Polo-box), proline-rich region binding (e.g. EVH1, SH3, GYF), acetylated lysine binding (e.g. Bromo), methylated lysine binding (e.g. Chromo, PHD), apoptosis (e.g. BIR, TRAF, DED, Death, CARD, BH), cytoskeleton modulation (e.g. ADF, GEL, DH, CH, FH2), ubiquitin-binding domains or modified or engineered versions thereof, or other cellular functions (e.g. EH, CC, VHL, TUDOR, PUF Repeat, PAS, MHI, LRRI, IQ, HEAT, GRIP, TUBBY, SNARE, TPR, TIR, START, SOCS Box, SAM, RGS, PDZ, PBI, LIM, F-BOX, ENTH, EF-Hand, SHADOW, ARM, ANK).

The enhancer domain typically increases or enhances the binding affinity for at least one or the target molecules. In some embodiments, the affinity may be increased by at least 10, 100 or 1000 fold compared to that of the recognition domain alone. The affinity clamp may further comprise linker connecting the recognition domain and the enhancer domain.

In one particular embodiment, the affinity clamp comprises a recognition domain that comprises at least a portion or fragment of a PDZ domain and an enhancer domain that comprises at least a portion or fragment of a fibronectin type III domain. The PDZ domain may be derived from a human Erbin protein. Erbin-PDZ (ePDZ) binds to target molecules such as the C-termini of p120-related catenins (such as δ-catenin and Armadillo repeat gene deleted in Velo-cardio-facial syndrome (ARVCF)). Preferably, this embodiment of the affinity claim further comprises the tenth ($10^{th}$) type III (FN3) domain of human fibronectin as an enhancer domain. Non-limiting examples of this embodiment are set forth in FIGS. 5 and 6

In some embodiments, the affinity clamp may comprise one or more connector amino acid sequences. For example, a connector amino acid sequence may connect the protease amino acid sequence (such as comprising a protease amino acid sequence) to the Erbin-PDZ domain, the Erbin-PDZ domain to the FN3 domain and/or the FN3 domain to the inhibitor.

Reference is also made to WO2009/062170, Zhuang & Liu, 2011, Comput. Theoret. Chem. 963 448, Huang et al, 2009, J. Mol. Biol. 392 1221 and Huang et al., 2008, PNAS (USA) 105 6578 for a more detailed explanation of affinity clamp structure and function.

In another embodiment, the first binding partner and/or the second binding partner amino acid sequences comprise one or a plurality epitopes that can be bind or be bound by an antibody target molecule.

In another embodiment, the first binding partner and/or second binding partners may be or comprise an antibody or antibody fragment, inclusive of monoclonal and polyclonal antibodies, recombinant antibodies, Fab and Fab'2 fragments, diabodies and single chain antibody fragments (e.g. scVs), although without limitation thereto. Suitably, the first and second binding partners may be or comprise respective antibodies or antibody fragments that bind a target molecule. Non-limiting examples are shown schematically in FIG. 2C.

In yet another particular embodiment, the first binding partner and/or second binding partner may be or comprise an antibody-binding molecule, wherein the antibody(ies) has specificity for a target molecule. The antibody-binding molecule is preferably an amino acid sequence of protein A, or a fragment thereof (e.g a ZZ domain), which binds an Fc portion of the antibody.

The subcomponent of the second molecular component may be or comprise a molecule capable of facilitating at least partial release of inhibition of the protease of the first molecular component by the inhibitor to switch the protease of the first molecular component from a protease inactive to a protease active state, or inhibition of the protease of the first molecular component by the inhibitor to switch the protease of the first molecular component from a protease active to a protease inactive state, upon a binding interaction between the first and second binding partners.

The subcomponent may be a molecule inclusive of proteins, peptides and fragments thereof, single- or duble-stranded nucleic acids such as DNA and RNA, lipids, sugars, oligosaccharides, polysaccharides and other carbohydrates and/or combinations of these. Broadly, the subcomponent of the second molecular component may comprise any molecule that was hereinbefore described as a first binding partner and/or a second binding partner, although without limitation thereto. Suitably, the first binding partner, second binding partner and the protein that is not a protease are different molecules or are different portions, parts, segments, domains, regions or fragments of the same molecule.

In one form of the invention, the subcomponent of the second molecular component comprises an amino acid sequence of any protein or fragment thereof.

In one broad embodiment, the amino acid sequence of the second molecular component is of a protein that is not a protease or protease fragment.

Suitably, according to this embodiment the first molecular component further comprises a cross-binder amino acid sequence. The cross-binder may be any molecule capable of binding the second molecular component. This includes single amino acids (e.g. natural or non-natural amino acids) and peptides inclusive of chemically modified amino acids and peptides, peptides modified to include non-natural amino acids, PNA, single or double-stranded nucleic acids inclusive of DNA or RNA aptamers, carbohydrates, lipids, lectins and/or binding agents such as biotin or avidin, although without limitation thereto. Suitably, the cross-binder is or comprises an amino acid or amino acid sequence fused, coupled, connected or contiguous with the protease inhibitor of the first molecular component. Typically, the cross-binder is located at or near the C-terminus of the first molecular component, although the cross-binder could be N-terminally located or located N-terminal and C-terminal of the protease inhibitor. Optionally, there is a linker amino acid sequence intermediate the cross-binder amino acid sequence and the protease inhibitor. As previously described, this amino acid sequence may be modified to include single- or double-stranded DNA, RNA, lipids, binding agents, chemical modifications to side chains etc.

Suitably, when the cross-binder is or comprises a peptide, it is typically of about 5-40 amino acids, preferably about 8 to about 30 amino acids or 12-20 amino acids in length.

Preferably, the cross-binder is capable of binding or interacting with the second molecular component, thereby facilitating: at least partial release of inhibition of the protease of the first molecular component by the inhibitor to switch the protease of the first molecular component from a protease inactive to a protease active state.

The cross-binder and the subcomponent of the second molecular component may bind or interact by way of any molecular interaction. Non-limiting examples include: a protein:protein interaction where the cross-binder is a peptide and the subcomponent of the second molecular component comprises an amino acid sequence of a protein or fragment thereof; a nucleic acid: nucleic acid interaction where the cross-binder and the subcomponent of the second molecular component comprise complementary nucleotide sequences; a biotin:avidin interaction wherein the cross-binder and the subcomponent of the second molecular component respectively comprise avidin and biotin or vice versa; and a lectin:carbohydrate interaction wherein the cross-binder and the subcomponent of the second molecular component respectively comprise a lectin and carbohydrate or vice versa, although without limitation thereto.

In one particular form of this embodiment, the subcomponent of the second molecular component comprises an amino acid sequence of calmodulin. According to this embodiment, the cross-binder of the first molecular component is a cross-binder of calmodulin. A non-limiting example is shown schematically in FIGS. 3 and 4. The cross-binder may be a calmodulin binding, myosin light chain kinase-derived peptide such as comprising the amino acid sequence RWKKNFIAVSAANRFKKISSSGAL (SEQ ID NO:16).

Figure 5:
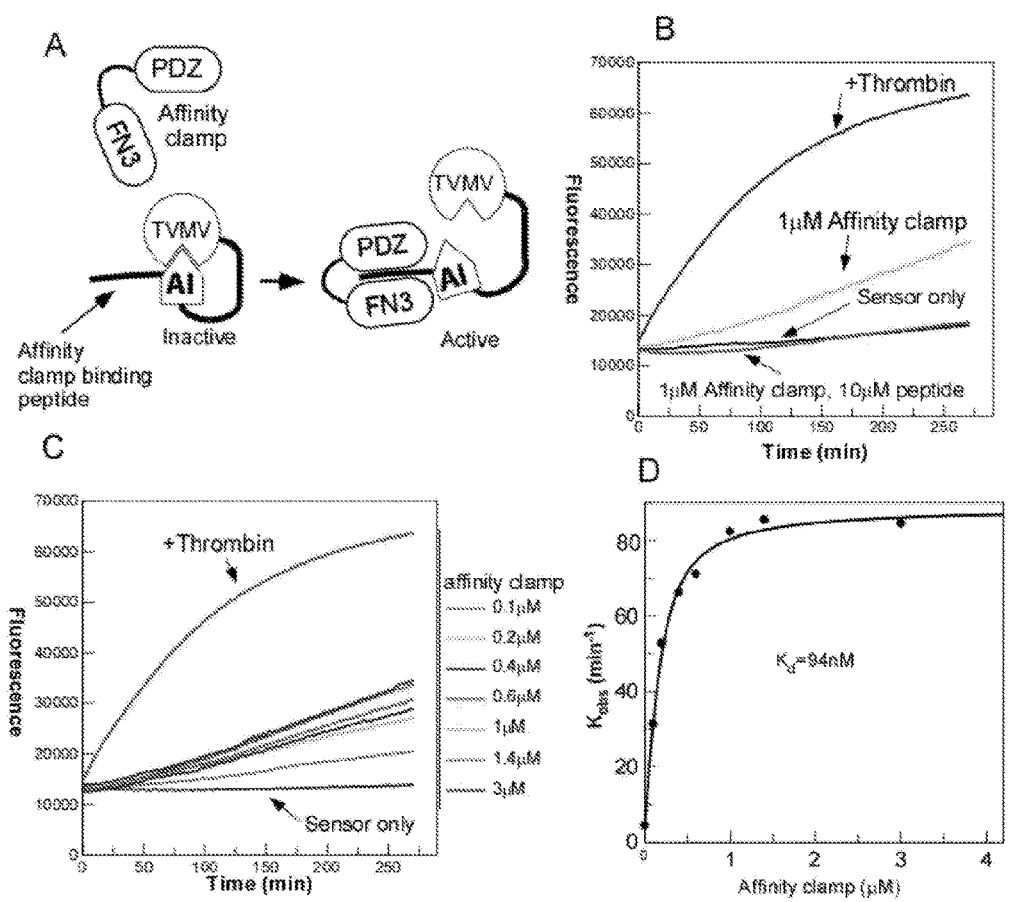
FIG. 5: Affinity clamp (PDZ-FN3)-induced TVMV protease biosensor activation via a cross-binder of affinity clamp (PDZ-FN3) fused to an autoinhibitor peptide (A)

In another particular form of this embodiment, the subcomponent of the second molecular component comprises an amino acid sequence of an affinity clamp as hereinbefore described. According to this embodiment, the cross-binder of the first molecular component is a cross-binder of the affinity clamp. The affinity clamp may be as hereinbefore described, such as an ePDZ-FN3 affinity clamp. A non-limiting example of this embodiment is shown in FIG. 5. The cross-binder may be or comprise a peptide corresponding to the C-terminal residues of ARVCF or δ-catenin (NH$_2$-PQPVDSWV-COOH: SEQ ID NO:17; and NH$_2$-PASPDSWV-COOH: SEQ ID NO:18, respectively). Preferably, the cross-binder is a peptide that comprises the amino acid sequence PQPVDSWV (SEQ ID NO:17)

Figure 3:
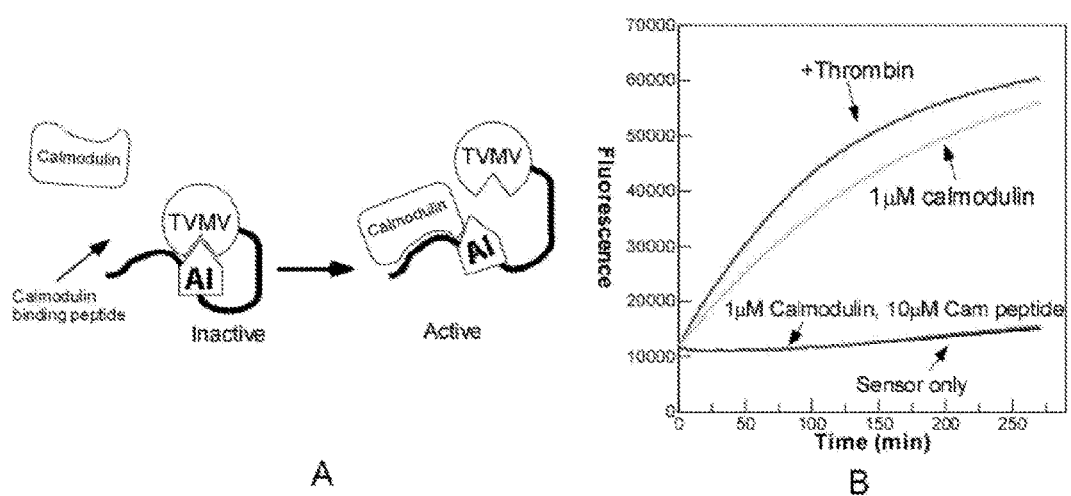
FIG. 3: Calmodulin-induced protease TVMV biosensor activation via a cross-binder of calmodulin fused to an autoinhibitor peptide. (A) schematic representation of the TVMV based calmodulin sensor comprised of TVMV protease, TVMV protease auto inhibitory peptide (AI) fused to the C-terminus of TVMV and calmodulin binding peptide fused to the C-terminus of AI. (B) Time trace of 1 μM TVMV-AI-calmodulin binder activity measured by degradation of fluorogenic TVMV substrate peptide in the presence of different concentrations of recombinant calmodulin, or calmodulin and calmodulin binding peptide (Cam). The time trace in the presence of thrombin represents a full activation of the construct due to cleavage of the sequence between TVMV and AI.

It will be appreciated that by addition of excess "free" cross-binder, it may displace the cross-binder of the first molecular component, thereby switching "off" or protease activity by allowing the inhibitor to rebind the protease of the first molecular component. An example of this is shown in FIG. 3.

Accordingly, in one preferred form the biosensor is a reversible biosensor.

In an alternative broad embodiment, the subcomponent of the second molecular component is of aprotease or protease fragment. Suitably, the protease of protease fragment of the second molecular component is other than the protease of the first molecular component. Suitably, the first molecular component further comprises at least one protease cleavage site cleavable by the protease of the second molecular component to release the protease-inhibitory effect of the inhibitor and thereby switch the first molecular component of the biosensor from a protease inactive to a protease active state.

Suitably, the at least one protease cleavage site is intermediate the protease amino acid sequence and the protease inhibitor.

In a further alternative embodiment, the first molecular component further comprises at least one protease cleavage site cleavable by said another protease of the second molecular component and the second molecular component further comprises at least one protease cleavage site cleavable by the protease of the first molecular component, whereby cleavage of the protease cleavage site of the first molecular component by the second protease releases the protease-inhibitory effect of the inhibitor to thereby switch the first molecular component of the biosensor from a protease inactive to a protease active state and cleavage of the protease cleavage site of the second molecular component by the protease of the first molecular component releases the protease-inhibitory effect of the inhibitor to thereby switch the first molecular component of the biosensor from a protease inactive to a protease active state.

Suitably, the at least one protease cleavage site in each of the first and second molecular components is intermediate the protease amino acid sequence and the protease inhibitor.

It will be appreciated that the protease and the protease inhibitor of the second molecular component may be as hereinbefore described for the first molecular component. Suitably, the protease and the protease inhibitor of the first molecular component is different to the protease and the protease inhibitor of the second molecular component. However, it will be appreciated that this broad embodiment may exploit or utilize a relatively low, constitutive or basal level of activity of the protease of the second molecular component second protease, or the respective proteases of both the first and second molecular components, even in the presence of inhibitors of either or both proteases.

In a particular embodiment, protease activation may be a consequence of "intramolecular swap" where the substrate sequences have affinities for respective active sites and may dislodge when in proximity. Suitably, it is the protease recognition sites that facilitate this "intramolecular swap". By way of example, the protease inhibitor of the first molecular component binds to an active site in the same position as the substrate peptide that is on the other protease. By increasing the local concentration of the substrate peptides then a spontaneously dissociated inhibitor peptide will be occasionally replaced by a substrate peptide which then will be cleaved. As the Kds of inhibitor peptides are in a high µM range the off rates are expected to be very high and hence this process is rapid. As cleavage makes reaction irreversible, it rapidly runs to completion In some embodiments, the second molecular component does not comprise an inhibitor of said another protease. Accordingly, the protease of the second molecular component is constitutively active (see for example FIG. 1C). Co-localization of the first and second molecular components upon binding or interaction between the first binding partner, the second binding partner and in some cases a target molecule, spatially localizes this basal or constitutive activity in the proximity of the first and/or second molecular components to thereby facilitate switching of the first protease and optionally the second protease, from an inactive to active state.

Accordingly, in the context of this embodiment, "switchable from a protease inactive to a protease active state" may include or mean an increase in protease activity from a less active state (e.g. rather than from completely inactive) to a substantially more active or fully active state. Alternatively, in the context of this embodiment, "switchable from a protease active to a protease inactive state" may include or mean a decrease in protease activity from an at least partly active state (e.g. rather than from completely active) to a substantially less active or substantially inactive state.

Suitably, the biosensor comprises a first molecular component that is a recombinant fusion protein and a second first molecular component that is a recombinant fusion protein. In some embodiments, the or each recombinant fusion protein comprises an affinity tag at a C-terminus thereof, which affinity tag facilitates isolation of biosensor molecules where protein translation has proceeded to the C-terminus of the protein product. The affinity tag suitably comprises an amino acid sequence of an epitope tag, fusion partner or other moiety that facilitates isolation and purification of the recombinant fusion protein.

Well known examples of fusion partners include, but are not limited to, glutathione-S-transferase (GST), maltose binding protein (MBP) and metal-binding moieties such as polyhistidine (e.g. $HIS_6$), for which affinity purification reagents are well known and readily available. Epitope tags are usually short peptide sequences for which a specific antibody is available. Well-known examples of epitope tags for which specific monoclonal antibodies are readily available include c-myc, influenza virus haemagglutinin and FLAG tags.

Preferably, the affinity tag is a C-terminal hexahistidine ($HIS_6$) tag.

Particular embodiments of the biosensor comprise first and/or second molecular components, cross-binders, subcomponents, proteases and/or protease inhibitors that comprise an amino acid sequence set forth in any one of SEQ ID NOS:1-18.

It will also be appreciated that the invention includes biosensors that comprise first and/or second molecular components, cross-binders, subcomponents, proteases and/or protease inhibitors that comprise amino acid sequences that are variants of the amino acid sequences set forth in SEQ ID NOS:1-18 and/or fragments thereof. Typically, such variants have at least 80%, at least 85%, at least 90%, 91%, 92%, 93%, 94% 95%96%, 97%, 98% or 99% sequence identity with any of the amino acid sequences set forth in SEQ ID NOS:1-18. By way of example only, conservative amino acid variations may be made without an appreciable or substantial change in function. For example, conservative amino acid substitutions may be tolerated where charge, hydrophilicity, hydrophobicity, side chain "bulk", secondary and/or tertiary structure (e.g. helicity), target molecule binding, protease activity and/or protease inhibitory activity are substantially unaltered or are altered to a degree that does not appreciably or substantially compromise the function of the biosensor and/or the first or second molecular components.

The term "sequence identity" is used herein in its broadest sense to include the number of exact amino acid matches having regard to an appropriate alignment using a standard algorithm, having regard to the extent that sequences are identical over a window of comparison. Sequence identity may be determined using computer algorithms such as GAP, BESTFIT, FASTA and the BLAST family of programs as for example disclosed by Altschul et al., 1997, Nucl. Acids Res. 25 3389. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999). Suitably, sequence identity is measured over the entire length of any one of SEQ ID NOS:1-18.

Protein fragments may comprise up to 5%, 10%, 15%, 200%, 25%, 30%, 35%, 40%, 45%, 50%, 55%, 60%, 65%, 70%, 75%, 80%, 85%, 90% or up to 95-99% of an amino acid sequence set forth in any one of SEQ ID NOS:1-18. In some embodiments, the protein fragment may comprise up to 5, 10, 15, 20, 30, 40, 50, 60, 70, 80, 90, 100, 120, 150, 180 200, 220, 230, 250, 280, 300, 320, 350, 400 or more amino acids of an amino acid sequence set forth in any one of SEQ ID NOS:1-18.

A further aspect of the invention provides a kit or composition comprising one or more biosensors disclosed herein in combination with one or more substrates.

The biosensor disclosed herein is particularly suitable for detection of a target molecule. The target molecule may be any molecule which can be detected by the first binding partner and the second binding partner of the biosensor, such as hereinbefore described.

Suitably, the substrate is a peptide which comprises a label.

As is well understood in the art, the label may be selected from a group including an enzyme, a fluorophore, a chemiluminescent molecule, biotin, radioisotope or other label.

Examples of suitable enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution or with a suitable chromogenic or chemiluminescent substrate.

Examples of chromogens include diaminobanzidine (DAB), permanent red, 3-ethylbenzthiazoline sulfonic acid (ABTS), 5-bromo-4-chloro-3-indolyl phosphate (BCIP), nitro blue tetrazolium (NBT), 3,3',5,5'-tetramethyl benzidine (TNB) and 4-chloro-1-naphthol (4-CN), although without limitation thereto.

A non-limiting example of a chemiluminescent substrate is Luminol™, which is oxidized in the presence of horseradish peroxidase and hydrogen peroxide to form an excited state product (3-aminophthalate).

Radioisotope labels may include $^{125}I$, $^{131}I$, $^{51}Cr$ and $^{99}Tc$, although without limitation thereto.

Fluorophores may be a coumarin, fluorescein isothiocyanate (FITC), tetramethylrhodamine isothiocyanate (TRITC), allophycocyanin (APC), Texas Red (TR), TAMRA, LC red, HEX, FAM, TET, ROX, Cy dyes such as Cy3 or Cy5 or R-Phycoerythrin (RPE) or derivatives thereof, although without limitation thereto.

Preferably, the label is a fluorophore. A preferred fluorophore is a coumarin such as 7-methoxycoumarin-4-acetic acid.

In a preferred embodiment where the label is a fluorophore, the substrate peptide may be quenched, whereby release of the fluorophore from quenching is detected as an increase in fluorescence signal. Non-limiting examples of quenchers include 5-amino-2-nitrobenzoic acid (ANA), Deep Dark Quenchers (DDQ), Iowa Black quenchers, Black Hole quenchers, Eclipse quenchers, Dabcyl and QSY quenchers which are commercially available from sources such as Eurogentec, Integrated DNA Technologies and Molecular Probes.

It will therefore be appreciated that in one embodiment, activation of the biosensor may be measured by the biosensor proteolytically cleaving a substrate, such as a fluorescently labeled peptide, to thereby facilitate detection of the presence of a target molecule in a sample.

According to this embodiment, the substrate peptide comprises a cleavage site specific to the protease of the biosensor. Preferably, detection of the label (e.g a fluorophore) occurs as a result of cleavage of the substrate.

In another embodiment, detection can be facilitated by one or more amplifier molecules.

According to this embodiment, activation of the biosensor may be measured by the biosensor proteolytically cleaving one or more amplifier molecules.

Accordingly, the invention provides a composition comprising one or more biosensors in combination with one or more amplifier molecules and one or more substrates for the amplifier molecule(s).

The amplifier molecule suitably comprises: (i) an amino acid sequence of at least a fragment of a protease that is different to the protease of the biosensor; (ii) an inhibitor of the protease of (i); and (iii) a linker amino acid sequence which comprises a cleavage site for the protease of the biosensor.

In this embodiment, the substrate peptide does not comprise a cleavage site for the protease(s) of the biosensor but comprises a cleavage site cleavable by the different protease of the amplifier molecule. Accordingly, the substrate peptide is not cleaved by activation of the protease of the biosensor. Rather, activation of the protease activity of the biosensor results in cleavage of the cleavage site in (iii) of the amplifier molecule, thereby releasing inhibition of the protease activity of the amplifier molecule.

Suitably, the substrate peptide of this embodiment comprises a cleavage site specific for the different protease of the amplifier molecule but which is not cleavable by the protease of the isolated sensor molecule.

In a particular embodiment, the biosensor may be linked or coupled to the amplifier molecule. For example, the biosensor and amplifier molecule may comprise respective interacting domains (i.e an amplifier interacting domain and a biosensor interacting domain) that facilitate releasable linking or coupling of the biosensor and amplifier molecules. Non-limiting examples of interacting domains include leucine zipper motifs, SH3:SH3 binding peptides, PDZ;PDZ-binding peptides, etc. The interacting domain could also be created by attaching the biosensor and the amplifier molecule to proteins or organic molecules capable of undergoing polymerisation or fibre formation.

In a further form of this embodiment, the composition may further comprise one or more deactivating molecules.

The deactivating molecule suitably comprises: (i) an amino acid sequence of a protease that is different to the protease of the biosensor and that is different to the protease of the amplifier molecule and different to the protease(s) of the biosensor; (ii) an inhibitor of the protease of (i); and (iii) a linker amino acid sequence which comprises a cleavage site for the protease of the amplification molecule.

According to this further form, activation of the protease activity of the amplification molecule results in the cleavage of the site in (iii) of the amplifier molecule, thereby releasing inhibition of the protease activity of the deactivating molecule. Suitably, the biosensor comprises one or more inactivating cleavage sites specific for the protease of the deactivating molecule. Accordingly, activation of the protease activity of the deactivating molecule results in cleavage of the inactivating cleavage site(s) which thereby substantially eliminates the protease activity of the biosensor.

It will therefore be appreciated that by manipulating the respective concentrations and/or activities of (a) the biosensor; (b) the amplifier molecule; and (c) the deactivating molecule, an appropriate level of signal amplification may be achieved to facilitate detection of the analyte.

It will be appreciated that in certain aspects, the biosensor disclosed herein may have efficacy in molecular diagnostics wherein the "target molecule" is an analyte or other molecule of diagnostic value or importance.

In a further aspect, the invention provides a method of detecting a target molecule, said method including the step of contacting the composition of the aforementioned aspect with a sample to thereby determine the presence or absence of the target molecule in the sample.

Suitably, the sample is a biological sample. Biological samples may include organ samples, tissue samples, cellular samples, fluid samples or any other sample obtainable, obtained, derivable or derived from an organism or a component of the organism. The biological sample can comprise a fermentation medium, feedstock or food product such as for example, but not limited to, dairy products.

In particular embodiments, the biological sample is obtainable from a mammal, preferably a human. By way of example, the biological sample may be a fluid sample such as blood, serum, plasma, urine, saliva, cerebrospinal fluid or amniotic fluid, a tissue sample such as a tissue or organ biopsy or may be a cellular sample such as a sample comprising red blood cells, lymphocytes, tumour cells or skin cells, although without limitation thereto. A particular type of biological sample is a pathology sample.

Suitably, the protease activity of the biosensor is not substantially inhibited by components of the sample (e.g. serum proteins, metabolites, cells, cellular debris and components, naturally-occurring protease inhibitors etc). Embodiments where the protease is of Potyvirus origin such as hereinbefore described may be particularly resistant to inhibition by components of human or mammalian biological samples.

In a particular embodiment, the method is for diagnosis of a disease or condition of an organism, inclusive of plants and animals. Animals may include fish, avians (e.g poultry) and mammals such as humans, livestock (e.g cattle and sheep), domestic pets (e.g. cats and dogs), performance animals (e.g. racehorses) and laboratory animals (e.g. rats, mice and rabbits), although without limitation thereto.

A preferred aspect of the invention provides a method of diagnosis of a disease or condition in a mammal, such as a human, said method including the step of contacting the composition of the aforementioned aspect with a biological sample obtained from the mammal or human to thereby determine the presence or absence of a target molecule in the biological sample, determination of the presence or absence of the target molecule facilitating diagnosis of the disease or condition.

The disease or condition may be any, where detection of a target molecule assists diagnosis. Non limiting examples of target molecules or analytes include blood coagulation factors such as previously described, kallikreins inclusive of PSA, matrix metalloproteinases, viral and bacterial proteases, antibodies, glucose, triglycerides, lipoproteins, cholesterol, tumour antigens, lymphocyte antigens, autoantigens and autoantibodies, drugs, drug precursors and drug metabolites, salts, creatinine, blood serum or plasma proteins, pesticides, uric acid, products and intermediates of human and animal metabolism and metals.

This preferred aspect of the invention may be adapted to be performed as a "point of care" method whereby determination of the presence or absence of the target molecule may occur at a patient location which is then either analysed at that location or transmitted to a remote location for diagnosis of the disease or condition.

One particular aspect of the invention therefore provides a device comprising the biosensor disclosed herein in a chamber or cell of the device and, optionally, an amplifier molecule. In some embodiments, the cell or chamber may be a component of, or connected or coupled to, a "point of care" device such as hereinbefore described.

Suitably, the cell or chamber is perfused with a sample and protease activity is detected.

In one form, the device may be for providing a disease diagnosis from a diagnostic test result, the device comprising:

a processor; and a memory coupled to the processor, the memory including computer readable program code components that, when executed by the processor, perform a set of functions including:

analysing a diagnostic test result and providing a diagnosis of the disease or condition.

The device may also be suitable for communicating a diagnostic test result, the device comprising:
   a processor; and
   a memory coupled to the processor, the memory including computer readable program code components that, when executed by the processor, perform a set of functions including:
   transmitting a diagnostic target result to a receiving device; and
   optionally receiving a diagnosis of the disease or condition from the or another receiving device.

The device may be in the form of a mobile or cellular phone, a computer or any other electronic device capable of analysing diagnostic target results at the "point of care" or transmitting and/or receiving information (i.e diagnostic target results and a disease diagnosis) to or from a receiving device at a remote location.

In one embodiment, protease activity is detected electrochemically. For example, detection may be by digesting a protein or peptide clot covering the surface of the electrode, whereby protease digestion of the clot enables access of an electrolyte to the electrode. In another example, activating the enzyme changes conductivity of a solution in the cell. In yet another example, the protease activity of the biosensor digests a conducting substrate and thereby changes conductivity. In a further example, the protease activity of the biosensor induces a substrate molecule or enzyme to become electrochemically active.

In another embodiment, protease activity is detected acoustically. For example, detection may be by measuring propagation of sound waves due to changes in viscosity of gels and solutions comprising one or more substrates of the protease.

In another embodiment, protease activity is detected optically. For example, detection may be by monitoring changes in reflection or refraction of light from surfaces comprising (e.g coated or impregnated with) one or more substrates of the protease.

A further embodiment of the invention relates to imaging of biological molecules. The activated protease activity of the biosensor cleaves a substrate peptide designed to change fluorescence and circulation time upon cleavage. This, for instance, may be brought about by the exposure of hydrophobic, or a cell-penetrating sequence and dequenching of a fluorophore. Alternatively the substrate peptide may be modified with a contrast substance such as metal (Ba) or an isotope for whole body imaging.

An advantage of the invention over the targeting of a particular tumour protease directly is in signal amplification and standardisation of the targeting peptide. Further the specificity of the response may be increased by targeting of the biosensor to a particular cell type or surface antigen by fusing or conjugating it to a targeting domain comprising a peptide, antibody or other targeting molecule.

In a further embodiment, the biosensor comprises first and second binding partners targeted to a particular type of surface molecule such as, for example, EGF receptor enriched in certain tumours. Activation of the proteolytic activity of the biosensor can be used for tumour visualisation or therapeutic targeting.

In a still further embodiment, an array of biosensors is connected or coupled to one or more electronic devices that utilise the "point of care" diagnostic device for identification of infective species. This embodiment is based on the observation that surface and secreted proteases play a key role in invasion and propagation of metazoan, bacterial and viral parasites. Each infective species can be categorized according to the unique protease signature. In a variation of the above described embodiment, the sensor array is composed of biosensors activated by metabolites and/or proteins of a parasitic organism.

Diagnostic aspects of the invention may also be in the form of a kit comprising one or a plurality of different biosensors capable of detecting one or a plurality of different target molecules. In this regard, a kit may comprise an array of different biosensors capable of detecting a plurality of different target molecules. The kit may further comprise one or more amplifier molecules, deactivating molecules and/or labeled substrates, as hereinbefore described. The kit may also comprise additional components including reagents such as buffers and diluents, reaction vessels and instructions for use.

A further aspect of the invention provides an isolated nucleic acid which encodes an amino acid sequence of the biosensor of the invention, or a variant thereof as hereinbefore defined.

The term "nucleic acid" as used herein designates single- or double-stranded mRNA, RNA, cRNA, RNAi, siRNA and DNA inclusive of cDNA, mitochondrial DNA (mtDNA) and genomic DNA.

A "polynucleotide" is a nucleic acid having eighty (80) or more contiguous nucleotides, while an "oligonucleotide" has less than eighty (80) contiguous nucleotides. A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™. A "probe" may be a single or double-stranded oligonucleotide or polynucleotide, suitably labelled for the purpose of detecting complementary sequences in Northern or Southern blotting, for example.

In particular embodiments, the isolated nucleic acid encodes an amino acid sequence selected from the group consisting of: SEQ ID NOS:1-18 or a fragment or variant thereof.

The invention also provides "genetic constructs" that comprise one or more isolated nucleic acids, variants or fragments thereof as disclosed herein operably linked to one or more additional nucleotide sequences.

As generally used herein, a "genetic construct" is an artificially created nucleic acid that incorporates, and/or facilitates use of, an isolated nucleic acid disclosed herein.

In particular embodiments, such constructs may be useful for recombinant manipulation, propagation, amplification, homologous recombination and/or expression of said isolated nucleic acid.

As used herein, a genetic construct used for recombinant protein expression is referred to as an "expression construct", wherein the isolated nucleic acid to be expressed is operably linked or operably connected to one or more additional nucleotide sequences in an expression vector.

An "expression vector" may be either a self-replicating extra-chromosomal vector such as a plasmid, or a vector that integrates into a host genome.

In this context, the one or more additional nucleotide sequences are regulatory nucleotide sequences.

By "operably linked" or "operably connected" is meant that said regulatory nucleotide sequence(s) is/are positioned relative to the nucleic acid to be expressed to initiate, regulate or otherwise control expression of the nucleic acid.

Regulatory nucleotide sequences will generally be appropriate for the host cell used for expression. Numerous types of appropriate expression vectors and suitable regulatory sequences are known in the art for a variety of host cells.

One or more regulatory nucleotide sequences may include, but are not limited to, promoter sequences, leader or signal sequences, ribosomal binding sites, transcriptional start and termination sequences, translational start and termination sequences, splice donor/acceptor sequences and enhancer or activator sequences.

Constitutive or inducible promoters as known in the art may be used and include, for example, nisin-inducible, tetracycline-repressible, IPTG-inducible, alcohol-inducible, acid-inducible and/or metal-inducible promoters.

In one embodiment, the expression vector comprises a selectable marker gene. Selectable markers are useful whether for the purposes of selection of transformed bacteria (such as bla, kanR, ermB and tetR) or transformed mammalian cells (such as hygromycin, G418 and puromycin resistance).

Suitable host cells for expression may be prokaryotic or eukaryotic, such as bacterial cells inclusive of *Escherichia coli* (DH5α for example), yeast cells such as *S. cerivisiae* or *Pichia pastoris*, insect cells such as SF9 cells utilized with a baculovirus expression system, or any of various mammalian or other animal host cells such as CHO, BHK or 293 cells, although without limitation thereto.

Introduction of expression constructs into suitable host cells may be by way of techniques including but not limited to electroporation, heat shock, calcium phosphate precipitation, DEAE dextran-mediated transfection, liposome-based transfection (e.g. lipofectin, lipofectamine), protoplast fusion, microinjection or microparticle bombardment, as are well known in the art.

Purification of the recombinant biosensor molecule may be performed by any method known in the art. In preferred embodiments, the recombinant biosensor molecule comprises a fusion partner (preferably a C-terminal His tag) which allows purification by virtue of an appropriate affinity matrix, which in the case of a His tag would be a nickel matrix or resin.

While many of the aforementioned aspects and embodiments relate to molecular diagnostics, it will also be appreciated that in certain aspects, the biosensor disclosed herein may have efficacy in cellular engineering where it is employed as extracellular, membrane, intracellular or nuclear receptor detecting a natural or synthetic ligand. Activation of the protease may be actuated on an effector comprising an enzymatic or structural protein domain operably linked to an auto inhibitory domain via a linker containing a cleavage site of the said protease. Such a protein domain may be a variant of a natural or synthetic protease, kinase, phosphatase, aminase, nuclease, scaffolding protein, structural protein, transcription factor or RNA binding protein, although without limitation thereto. Activation of the said effect may regulate a natural or synthetic enzymatic, metabolic or signalling cascade modulating cellular processes such as cellular proliferation, migration, biosynthesis survival, differentiation or death, although without limitation thereto So that the invention may be readily understood and put into practical effect, embodiments of the invention will be described with reference to the following non-limiting Examples.

EXAMPLES

Example 1

Calmodulin-Activated Protease Sensor

In this embodiment a biosensor comprises an autoinhibited TVMV protease where the autoinhibitory peptide is fused to an amino acid sequence of a calmodulin binder via a linker amino acid sequence as shown in FIG. 3. Calmodulin sterically competes for and binds the calmodulin binder, thereby releasing inhibition of the TVMV protease by the autoinhibitor peptide. This is shown in FIG. 3. Addition of "free" calmodulin binder displaces the calmodulin binder from calmodulin, thereby allowing the autoinhibitory peptide to bind and inhibit the TVMV protease.
Protein Sequence for Calmodulin Activated Sensor:

```
TVMV-AI-CalmodulinBinder
                                         (SEQ ID NO: 1)
SKALLKGVRDFNPISACVCLLENSSDGHSERLFGIGFGPYIIANQHLFRR

NNGELTIKTMHGEFKVKNSTQLQMKPVEGRDIIVIKMAKDFPPFPQKLKF

RQPTIKDRVCMVSTNFQQKSVSSLVSESSHIVHKEDTSFWQHWITTKDGQ

CGSPLVSIIDGNILGIHSLTHTTNGSNYFVEFPEKFVATYLDAADGWCKN

WKFNADKISWGSFILWEDAPEDFMSGLVPRGVGREYVRFAPRWKKNFIAV

SAANRFKKISSSGAL

Calmodulin
                                         (SEQ ID NO: 2)
SGQLTEEQIAEFKEAFSLFDKDGDGTITTKELGTVMRSLGQNPTEAELQD

MINEVDADGNGTIDFPEFLTMMARKMKDTDSEEEIREAFRVFDKDGNGYI

SAAELRHVMTNLGEKLTDEEVDEMIREADIDGDGQVNYEEFVQMMTAK
```

Example 2

Calmodulin Activated Reversible Two Component Biosensor

Figure 4:
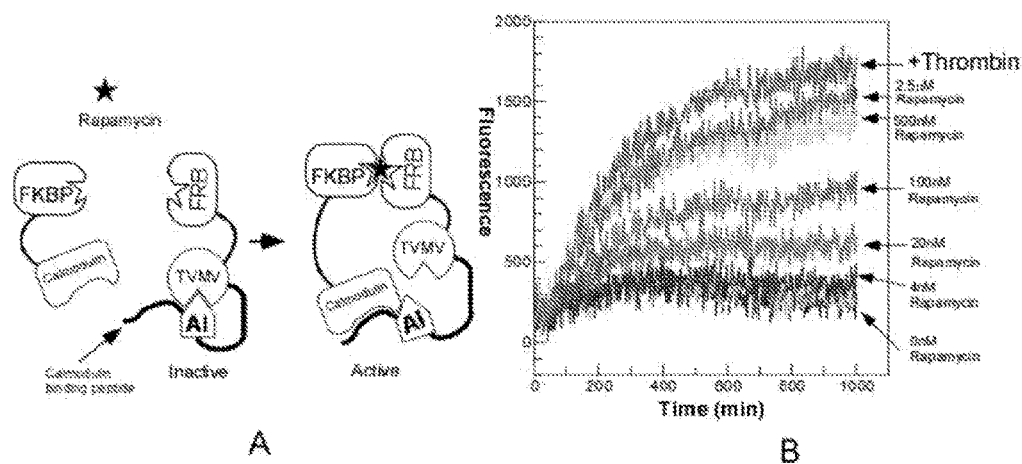
FIG. 4: Two component calmodulin activated system (A) A rapamycin-binding two-component biosensor comprising: a first molecular component comprising TVMV protease fused to a cross-binder of calmodulin, an autoinhibitor peptide and rapamycin-binding FRB; and a second molecular component comprising calmodulin fused to rapamycin-binding FKBP12; (B) activity analysis of FRB-TVMV-AI-binder fusion by itself, in the presence of increasing concentrations of rapamycin. Thrombin cleaves the protein between TVMV and AI. Assays were performed as in FIG. 3.

In this embodiment the two-component biosensor comprises a first molecular component having an autoinhibited TVMV protease where the autoinhibitory peptide is fused to an amino acid sequence of a calmodulin binder via a linker amino acid sequence as shown in FIG. 4. The TVMV amino acid sequence is fused to an FRB amino acid sequence via a linker amino acid sequence. The second molecular component is calmodulin coupled via a linker amino acid sequence to an FKBP12 amino acid sequence. Addition of rapamycin causes localization of the first and second molecular components through binding of rapamycin by FRB and FKBP12. The calmodulin binder of the first molecular component binds calmodulin of the second molecular component, thereby releasing inhibition of the TVMV protease by the autoinhibitor peptide. This is shown in FIG. 4. Addition of "free" calmodulin binder displaces the calmodulin binder from calmodulin, thereby allowing the autoinhibitory peptide to again bind and inhibit the TVMV protease.

Assay Conditions:
1. Assay buffer: 50 mM Tris/HCl pH 8, 50 mM NaCl, 2 mM DTT, 50 µg/mL BSA, 3 mM $CaCl_2$, (Ca is not present in the positive control, in which sample the thrombin was added to activate TVMV fully)
2. Final assay volume: 200 µL
3. FRB-TVMV-AI-CalmodulinBinder: 0.5 nM
4. FKBP12-Calmodulin: 50 nM
5. Thrombin: 1U
6. TVMV substrate: 1 µM
7. TVMV substrate: ANA-GETVRFQSGT-164-$NH_2$
   ANA: 5-amino-2-nitrobenzoyl group
   164: refers to a Mimotopes specific code for lysince coupled to a 7-methoxycoumarinyl-4-acetyl group The plate reader (Biotek Synergy 4) was used at exitation wavelength 330 nm and emission wavelength 405 nm.
Protein Sequence for Two Component Calmodulin System:

FRB-TVMV-AI-CalmodulinBinder:
(SEQ ID NO: 3)
GGVAILWHEMWHEGLEEASRLYFGERNVKGMFEVLEPLHAMMERGPQTL

KETSFNQAYGRDLMEAQEWCRKYMKSGNVKDLTQAWDLYYHVFRRISGG

SKALLKGVRDFNPISACVCLLENSSDGHSERLFGIGFGPYIIANQHLFR

RNNGELTIKTMHGEFKVKNSTQLQMKPVEGRDIIVIKMAKDFPPFPQKL

KFRQPTIKDRVCMVSTNFQQKSVSSLVSESSHIVHKEDTSFWQHWITTK

DGQCGSPLVSIIDGNILGIHSLTHTTNGSNYFVEFPEKFVATYLDAADG

WCKNWKFNADKISWGSFILWEDAPEDFMSGLVPRGVGREYVRFAPRWKK

NFIAVSAANRFKKISSSGAL

FKBP12-Calmodulin:
(SEQ ID NO: 4)
GTGVQVETISPGDGRTFPKRGQTCVVHYTGMLEDGKKFDSSRDRNKPFKF

MLGKQEVIRGWEEGVAQMSVGQRAKLTISPDYAYGATGHPGIIPPHATIV

FDVELLKLEGGSGGSGGQLTEEQIAEFKEAFSLFDKDGDGTITTKELGTV

MRSLGQNPTEAELQDMINEVDADGNGTIDFPEFLTMMARKMKDTDSEEEI

REAFRVFDKDGNGYISAAELRHVMTNLGEKLTDEEVDEMIREADIDGDGQ

VNYEEFVQMMTAK

Example 3

Affinity Clamp-Activated Protease Sensor

In this embodiment the biosensor comprises an autoinhibited TVMV protease where the autoinhibitory peptide is fused to an amino acid sequence of an ePDZ-FN3 binder via a linker amino acid sequence as shown in FIG. 5. Addition of ePDZ causes the ePDZ binder of the first molecular component to bind ePDZ, thereby releasing inhibition of the TVMV protease by the autoinhibitor peptide. This is shown in FIG. 5.
Sequence of the Affinity Clamp-Activated Protease Sensor TVMV-AI-ePDZ-Binder
(SEQ ID NO: 5)
SKALLKGVRDFNPISACVCLLENSSDGHSERLFGIGFGPYIIANQHLFR

RNNGELTIKTMHGEFKVKNSTQLQMKPVEGRDIIVIKMAKDEPPFPQKL

KFRQPTIKDRVCMVSTNFQQKSVSSINSESSHIVHKEDTSFWQHWITTK

DGQCGSPLVSIIDGNILGIHSLTHTTNGSNYFVEFPEKFVATYLDAADG

WCKNWKFNADKISWGSFILWEDAPEDFMSGLVPRGVGREYVRFAPGGPQ

PVDSWV ePDZ
(SEQ ID NO: 6)
SGTSPELGFSISGGVGGRGNPFRPDDDGIFVTRVQPEGPASKLLQPGDK

IIQANGYSFINIEHGQAVSLLKTFQNTVELIIVREVGNGAKQEIRVRVE

KDGGSGGVSSVPTNLEVVAATPTSLLISWDASYYGVSYYRITYGETGGN

SPVQEFTVPYSSSTATISGLKPGVDYTITVYAYSDYYGSHHYSPISINY

RTSGC

Example 4

Two Component Affinity Clamp-Activated Protease Sensor

Figure 6:
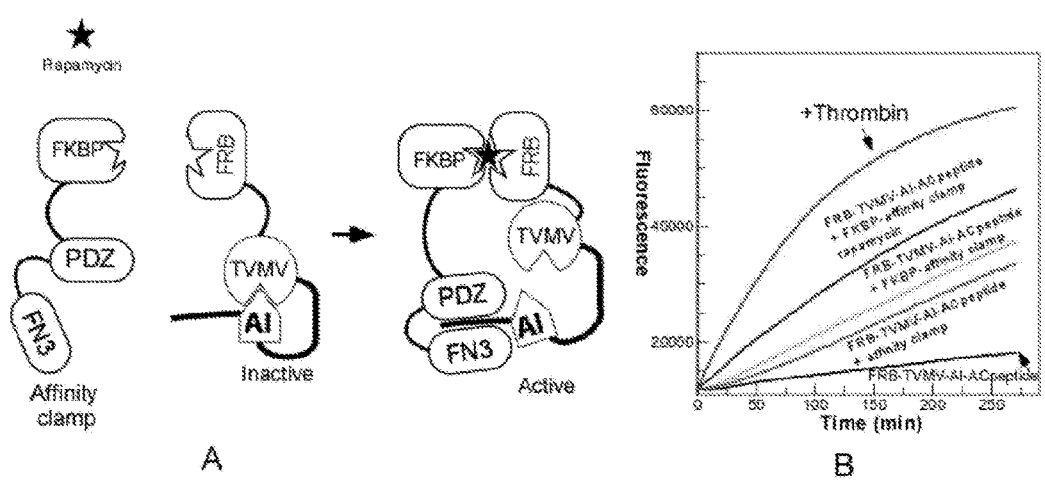

In this embodiment the two-component biosensor comprises a first molecular component having an autoinhibited TVMV protease where the autoinhibitory peptide is fused to an amino acid sequence of a calmodulin binder via a linker amino acid sequence as shown in FIG. 6. The TVMV amino acid sequence is fused to an FRB amino acid sequence via a linker amino acid sequence. The second molecular component is ePDZ-FN3 coupled via a linker amino acid sequence to an FKBP12 amino acid sequence. Addition of rapamycin causes localization of the first and second molecular components through binding of rapamycin by FRB and FKBP12. The ePDZ-FN3 binder of the first molecular component binds ePDZ of the second molecular component, thereby releasing inhibition of the TVMV protease by the autoinhibitor peptide. This is shown in FIG. 6.
Assay Conditions:
1. Assay buffer: 50 mM Tris/HCl pH 8, 50 mM NaCl, 2 mM DTT, 50 µg/mL BSA
2. Final assay volume: 200 µL
3. FRB-TVMV-AI-ePDZ-Binder: 1 µM
4. FKBP12-ePDZ: 1 µM
5. Thrombin: 1U
6. TVMV substrate: 10 µM
7. TVMV substrate: ANA-GETVRFQSGT-164-NH2
   ANA: 5-amino-2-nitrobenzoyl group
   164: refers to a Mimotopes specific code for lysince coupled to a 7-methoxycoumarinyl-4-acetyl group The plate reader (Biotek Synergy 4) was used at exitation wavelength 330 nm and emission wavelength 405 nm.
Protein Sequence for Affinity Clamp System:

FRB-TVMV-AI-ePDZ-Binder:
(SEQ ID NO: 7)
GGVAILWHEMWHEGLEEASRLYFGERNVKGMFEVLEPLHAMMERGPQTL

KETSFNQAYGRDLMEAQEWCRKYMKSGNVKDLTQAWDLYYHVFRRISGG

SKALLKGVRDFNPISACVCLLENSSDGHSERLFGIGFGPYIIANQHLFRR

NNGELTIKTMHGEFKVKNSTQLQMKPVEGRDIIVIKMAKDFPPFPQKLKF

RQPTIKDRVCMVSTNFQQKSVSSLYSESSHIVHKEDTSFWQHWITTKDGQ

CGSPLVSIIDGNILGIFISLTHTTNGSNYFVEFPEKFVATYLDAADGWCK

NWKFNADKISWGSFILWEDAPEDFMSGLVPRGVGREYVRFAPGGPQPVDS

WV

FKBP12-ePIDZ:
(SEQ ID NO: 8)
GTGVQVETISPGDGRTFPKRGQTCVVHYTGMLEDGKKFDSSRDRNKPFKF

MLGKQEVIRGWEEGVAQMSVGQRAKLTISPDYAYGATGHPGIIPPHATLV

FDVELLKLEGGSGGSGGSPELGFSISGGVGGRGNPFRPDDDGIFVTRVQP

EGPASKLLQPGDKIIQANGYSFINIEHGQAVSLLKTFQNTVELIIVREVG

NGAKQEIRVRVEKDGGSGGVSSVPTNLEVVAATPTSLLISWDASYYGVSY

YRITYGETGGNSPVQEFTVPYSSSTATISGLKPGVDYTITVYAYSDYYGS

HHYSPISINYRTSGC

Example 5

Two Component Rapamycin Activated Protease Sensor

Figure 7:
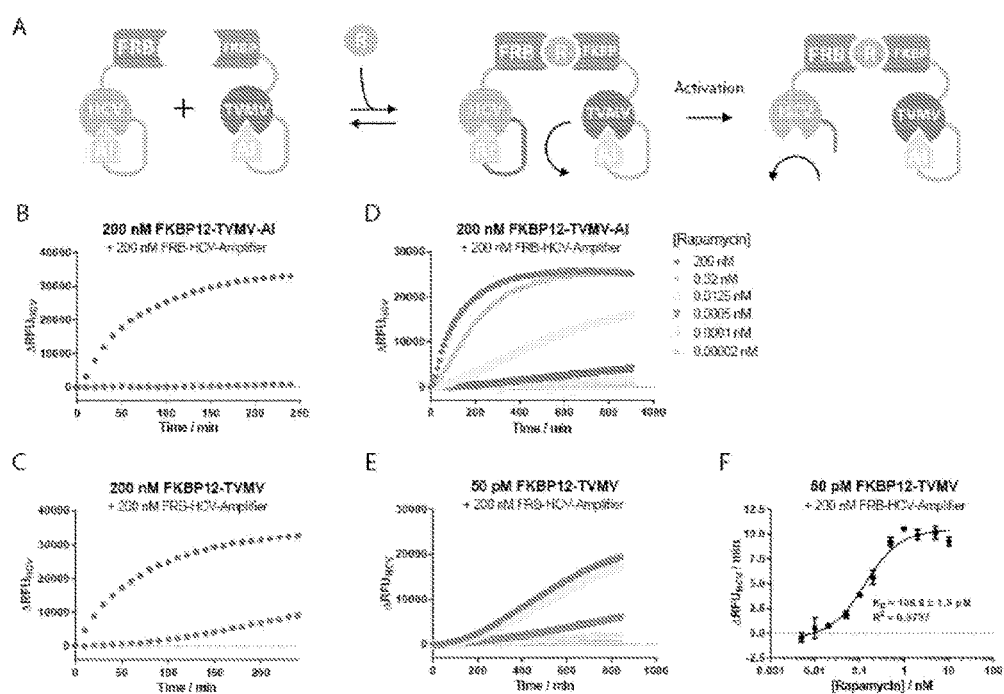
Figure 8:
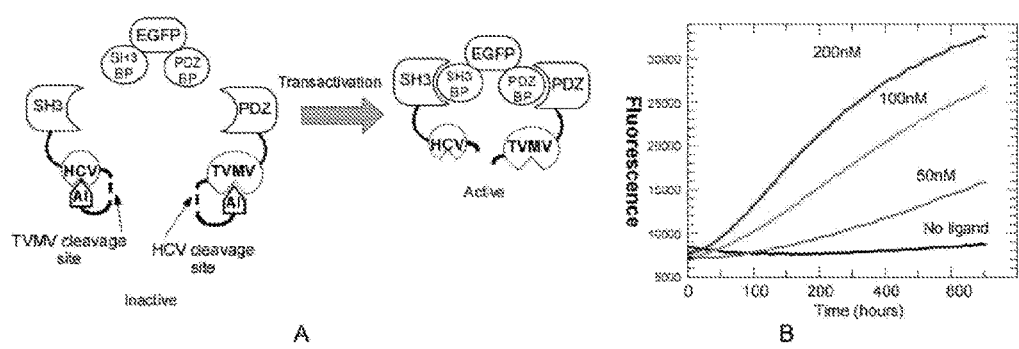

Referring to FIG. 7A, the principle is to design autoinhibited protease-based proximity sensors. A TVMV-inducible mutant of HCV was fused to FRB and a thrombin-inducible mutant of TVMV was fused to FKBP12. In the presence of rapamycin, TVMV co-localizes with HCV resulting in rapid cleavage of the latter. (FIG. 7 B, C) Time resolved traces of protease activities of HCV activity of the sensors in the absence (red) or presence (blue) of rapamycin. Note that background activation is significantly reduced in the presence of the AI-domain (D, E). Titration of rapamycin to the two component sensor induces HCV activation at sub pM concentrations. (F). Quantification of Kds for rapamycin for uninhibited TVMV at different ligand concentrations. Proteases were assayed with 5 μM quenched fluorescent substrate peptide.

Protein Sequence for Activated Protease Sensor

FKBP12-TVMV$^{Thr}$-AI:
(SEQ ID NO: 9)
GGSGGSGGVQVETISPGDGRTFPKRGQTCVVHYTGMLEDGKKFDSS

RDRNKPFKFMLGKQEVIRGWEEGVAQMSVGQRAKLTISPDYAYGA

TGHPGIIPPHATLVFDVELLKLEGGSGGSGGSGGSGGSGGSKALLKGV

RDFNPISACVCLLENSSDGHSERLFGIGFGPYIIANQHLFRRNNGELTI

KTMHGEFKNSTQLQMKPVEGRDIIVIKMAKDFPPFPQKLKFRQPTIKDR

VCMVSTNFQQKSVSSLVSESSHIVHKEDTSFWQHWITTKDGQCGSPLVSI

IDGNILGIHSLTHTTNGSNYFVEFPEKFVATYLDAADGWCKNWKFNAD

KISWGSFILWEDAPEDFMSGLVPRGVGREYVRFAPGSTHHHHHH

HCV$^{TVMV}$-AI-FRB:

(SEQ ID NO: 10)

SMSTSGSGSGSAKGSVVIVGRINLSGDTAYSQQTRGAAGIAATSATGRD

KNQVDGEVQVLSTATQSFLATCVNGVCWTVYHGAGSKTLAGPKGPITQ

MYTNVDQDLVGWPAPPGARSMTPCTCGSSDLYLVTRHADVIPVRRRGD

SRGSLLSPRPVSYLKGSSGGPLLCPSGHVVGIFRAAVCTRGVAKAVDFIP

VESMETTMRGGSGGSGGETVRFQSGGSGGDELILCPLDLGGSGGSGGS

GGGSGGSGGVAILWHEMWREGLEEASRLYFGERNVKGMFEVLEPL

HAMMERGPQTLKETSFNQAYGRDLMEAQEWCRKYMKSGNVKDL

TQAWDLYYHVFRRIGGTGHHHHHH

Example 6

Dual Specificity Two Component Biosensor

This embodiment of the two-component biosensor is capable of binding different portions of the same target molecule. As shown in FIG. 8, the first molecular component is a fusion protein that comprises an SH3 domain binding partner, HCV protease, a linker containing a TVMV protease cleavage site an autoinhibitor of the HCV protease. The second molecular component is a fusion protein that comprises a PDZ domain binding partner, TVMV protease, a linker containing a HCV protease cleavage site an autoinhibitor of the TVMV protease. As shown in FIG. 8, the target molecule comprises EGFP N-terminally fused to a ligand for an SH3 domain binding partner and C-terminally fused to a ligand for a PDZ domain binding partner. The binding of the target molecule by the respective binding partners causes co-localization of the first and second molecular components. The TVMV and HCV proteases have a basal level of protease activity notwithstanding presence of their respective inhibitors, resulting in reciprocal cleavage of the TVMV and HCV protease cleavage sites, thereby more fully activating both proteases. The data showing this reciprocal activation is shown in FIG. 8. It is possible that protease activation is a consequence of "intramolecular swap" where the substrate sequences that have affinities for respective active sites and relocate there when in proximity. Suitably, it is the protease recognition sites that facilitate this "intramolecular swap". By way of example, the protease inhibitor of the first molecular component binds to an active site in the same position as the substrate peptide that is on the other protease. By increasing the local concentration of the substrate peptides then a spontaneously dissociated inhibitor peptide will be occasionally replaced by a substrate peptide which then will be cleaved. As the Kds of inhibitor peptides are in a high mM range the off rates are expected to be very high and hence this process is rapid. As cleavage makes reaction irreversible, it rapidly runs to completion.

Assay Conditions:

1. Buffer: 100 mM Tris, 30 mM NaCl, 2 mM DTT, 50 μg/mL BSA, pH 8.0
2. Titration of ligands into cascade: 200 nM of HCV based protease and 200 nM of TVMV based protease.
3. Final assay volume: 200 μL. Pre-incubate ligand with TVMV based protease. Add 10 μM of HCV substrate (quenched fluorescent peptide) at last step to initiate.
4. Concentrations of ligands for titration: 0 nM, 50 nM, 100 nM and 200 nM Sequences of Fusion Proteins Containing Binding Peptides SH3$^{pep}$-EGFP-PDZ$^{pep}$:

(SEQ ID NO: 11)

MAHHHHHHSSGGSPPPPLPPKRRRGGSGGSGGVSKGEELFTGVVPILVEL

DGDVNGHKFSVSGEGEGDATYGKLTLKFICTTGKLPVPWPTLVTTLTYGV

QCFSRYPDHMKQHDFFKSAMPEGYVQERTIFFKDDGNYKTRAEVKFEGDT

LVNRIELKGIDFKEDGNILGHKLEYNYNSHNVYIMADKQKNGIKVNFKIR

HNIEDGSVQLADHYQQNTPIGDGPVLLPDNIHYLSTQSALSKDPNEKRDH

MVLLEFVTAAGITLGMDELYKGGSGGSGGPQPVDSWV

MBP-SH3$^{pep}$-PDZ$^{pep}$:

(SEQ ID NO: 12)

MENAQKGEIMPNIPQMSAFWYAVRTAVINAASGRQTVDEALKDAQTNSSS

NNNNNNNNNNLGIEGRGENLYFQSGGHHHHHHGGSGGPPPPLPPKRRRGG

SGGSGGPQPVDSWV

SH3$^{pep}$-PDZ$^{pep}$ peptide:

(SEQ ID NO: 13)

PPPPLPPKRRRGGSGGPQPVDSWV

Sequences of HCV and TVMV Based Proteases

HCV-SH3$^{dom}$ with C-terminal TVMV-inducible AI-domain (SEQ ID NO: 14)

MENAQKGEIMPNIPQMSAFWYAVRTAVINAASGRQTVDEALKDAQTNSSS

NNNNNNNNNNLGIEGRGDDVTPCSMSTSGSGGAEYVRALFDFNGNDEEDL

PFKKGDILRIRDKREEQWWNAEDSEGKRGMPPVPYVEKYRPASASVSALI

GGRGGSGGSGGSGGSGGSGGSAKGSVVIVGRINESGDTAYSQQTRGAAGI

AATSATGRDKNQVDGEVQVLSTATQSFLATCVNGVCWTVYHGAGSKTLAG

PKGPITQMYTNVDQDLVGWPAPPGARSMTPCTCGSSDLYLVTRHADVIPV

RRRGDSRGSLLSPRPVSYLKGSSGGPLLCPSGHVVGIFRAAVCTRGVAKA

VDFIPVESMETTMRGGGSGGETVRFQSGGSGGDELILCPLDLGGSGGTG

HHHHHH

TVMV-PDZ$^{dom}$ with C-terminal HCV-inducible AI-domain
(SEQ ID NO: 15

Ser Gly Leu Val Pro Arg Gly Val Gly Arg Glu Tyr Val Arg Phe Ala
225                 230                 235                 240

Pro Arg Trp Lys Lys Asn Phe Ile Ala Val Ser Ala Ala Asn Arg Phe
            245                 250                 255

Lys Lys Ile Ser Ser Ser Gly Ala Leu
        260                 265

<210> SEQ ID NO 2
<211> LENGTH: 148
<212> TYPE: PRT
<213> ORGANISM: Homo sapiens

<400> SEQUENCE: 2

Ser Gly Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 3
<211> LENGTH: 363
<212> TYPE: PRT
<213> ORGANISM: Artificial sequence
<220> FEATURE:
<223> OTHER INFORMATION: Calmodulin Binder Construct

<400> SEQUENCE: 3

Gly Gly Val Ala Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
65                  70                  75                  80

Leu Thr Gln Ala Trp Asp Leu Tyr Tyr His Val Phe Arg Arg Ile Ser
                85                  90                  95

Gly Gly Ser Lys Ala Leu Leu Lys Gly Val Arg Asp Phe Asn Pro Ile
            100                 105                 110

```
Ser Ala Cys Val Cys Leu Leu Glu Asn Ser Ser Asp Gly His Ser Glu
        115                 120                 125

Arg Leu Phe Gly Ile Gly Phe Gly Pro Tyr Ile Ile Ala Asn Gln His
    130                 135                 140

Leu Phe Arg Arg Asn Asn Gly Glu Leu Thr Ile Lys Thr Met His Gly
145                 150                 155                 160

Glu Phe Lys Val Lys Asn Ser Thr Gln Leu Gln Met Lys Pro Val Glu
                165                 170                 175

Gly Arg Asp Ile Ile Val Ile Lys Met Ala Lys Asp Phe Pro Pro Phe
            180                 185                 190

Pro Gln Lys Leu Lys Phe Arg Gln Pro Thr Ile Lys Asp Arg Val Cys
        195                 200                 205

Met Val Ser Thr Asn Phe Gln Gln Lys Ser Val Ser Ser Leu Val Ser
    210                 215                 220

Glu Ser Ser His Ile Val His Lys Glu Asp Thr Ser Phe Trp Gln His
225                 230                 235                 240

Trp Ile Thr Thr Lys Asp Gly Gln Cys Gly Ser Pro Leu Val Ser Ile
                245                 250                 255

Ile Asp Gly Asn Ile Leu Gly Ile His Ser Leu Thr His Thr Thr Asn
            260                 265                 270

Gly Ser Asn Tyr Phe Val Glu Phe Pro Glu Lys Phe Val Ala Thr Tyr
        275                 280                 285

Leu Asp Ala Ala Asp Gly Trp Cys Lys Asn Trp Lys Phe Asn Ala Asp
    290                 295                 300

Lys Ile Ser Trp Gly Ser Phe Ile Leu Trp Glu Asp Ala Pro Glu Asp
305                 310                 315                 320

Phe Met Ser Gly Leu Val Pro Arg Gly Val Gly Arg Glu Tyr Val Arg
                325                 330                 335

Phe Ala Pro Arg Trp Lys Lys Asn Phe Ile Ala Val Ser Ala Ala Asn
            340                 345                 350

Arg Phe Lys Lys Ile Ser Ser Ser Gly Ala Leu
        355                 360

<210> SEQ ID NO 4
<211> LENGTH: 263
<212> TYPE: PRT
<213> ORGANISM: Artificial sequence
<220> FEATURE:
<223> OTHER INFORMATION: FKBP12-Calmodulin chimera

<400> SEQUENCE: 4

Gly Thr Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
            20                  25                  30

Glu Asp Gly Lys Lys Phe Asp Ser Ser Arg Asp Arg Asn Lys Pro Phe
        35                  40                  45

Lys Phe Met Leu Gly Lys Gln Glu Val Ile Arg Gly Trp Glu Glu Gly
    50                  55                  60

Val Ala Gln Met Ser Val Gly Gln Arg Ala Lys Leu Thr Ile Ser Pro
65                  70                  75                  80

Asp Tyr Ala Tyr Gly Ala Thr Gly His Pro Gly Ile Ile Pro Pro His
                85                  90                  95

Ala Thr Leu Val Phe Asp Val Glu Leu Leu Lys Leu Glu Gly Gly Ser
            100                 105                 110
```

-continued

```
Gly Gly Ser Gly Gly Gln Leu Thr Glu Glu Gln Ile Ala Glu Phe Lys
            115                 120                 125
Glu Ala Phe Ser Leu Phe Asp Lys Asp Gly Asp Gly Thr Ile Thr Thr
        130                 135                 140
Lys Glu Leu Gly Thr Val Met Arg Ser Leu Gly Gln Asn Pro Thr Glu
145                 150                 155                 160
Ala Glu Leu Gln Asp Met Ile Asn Glu Val Asp Ala Asp Gly Asn Gly
                165                 170                 175
Thr Ile Asp Phe Pro Glu Phe Leu Thr Met Met Ala Arg Lys Met Lys
            180                 185                 190
Asp Thr Asp Ser Glu Glu Glu Ile Arg Glu Ala Phe Arg Val Phe Asp
        195                 200                 205
Lys Asp Gly Asn Gly Tyr Ile Ser Ala Ala Glu Leu Arg His Val Met
210                 215                 220
Thr Asn Leu Gly Glu Lys Leu Thr Asp Glu Glu Val Asp Glu Met Ile
225                 230                 235                 240
Arg Glu Ala Asp Ile Asp Gly Asp Gly Gln Val Asn Tyr Glu Glu Phe
                245                 250                 255
Val Gln Met Met Thr Ala Lys
            260

<210> SEQ ID NO 5
<211> LENGTH: 251
<212> TYPE: PRT
<213> ORGANISM: Artificial sequence
<220> FEATURE:
<223> OTHER INFORMATION: Chimeric binder construct

<400> SEQUENCE: 5

Ser Lys Ala Leu Leu Lys Gly Val Arg Asp Phe Asn Pro Ile Ser Ala
1               5                   10                  15
Cys Val Cys Leu Leu Glu Asn Ser Ser Asp Gly His Ser Glu Arg Leu
            20                  25                  30
Phe Gly Ile Gly Phe Gly Pro Tyr Ile Ile Ala Asn Gln His Leu Phe
        35                  40                  45
Arg Arg Asn Asn Gly Glu Leu Thr Ile Lys Thr Met His Gly Glu Phe
    50                  55                  60
Lys Val Lys Asn Ser Thr Gln Leu Gln Met Lys Pro Val Glu Gly Arg
65                  70                  75                  80
Asp Ile Ile Val Ile Lys Met Ala Lys Asp Phe Pro Pro Phe Pro Gln
                85                  90                  95
Lys Leu Lys Phe Arg Gln Pro Thr Ile Lys Asp Arg Val Cys Met Val
            100                 105                 110
Ser Thr Asn Phe Gln Gln Lys Ser Val Ser Ser Leu Val Ser Glu Ser
        115                 120                 125
Ser His Ile Val His Lys Glu Asp Thr Ser Phe Trp Gln His Trp Ile
    130                 135                 140
Thr Thr Lys Asp Gly Gln Cys Gly Ser Pro Leu Val Ser Ile Ile Asp
145                 150                 155                 160
Gly Asn Ile Leu Gly Ile His Ser Leu Thr His Thr Thr Asn Gly Ser
                165                 170                 175
Asn Tyr Phe Val Glu Phe Pro Glu Lys Phe Val Ala Thr Tyr Leu Asp
            180                 185                 190
Ala Ala Asp Gly Trp Cys Lys Asn Trp Lys Phe Asn Ala Asp Lys Ile
        195                 200                 205
```

```
Ser Trp Gly Ser Phe Ile Leu Trp Glu Asp Ala Pro Glu Asp Phe Met
    210                 215                 220

Ser Gly Leu Val Pro Arg Gly Val Gly Arg Glu Tyr Val Arg Phe Ala
225                 230                 235                 240

Pro Gly Gly Pro Gln Pro Val Asp Ser Trp Val
                245                 250

<210> SEQ ID NO 6
<211> LENGTH: 201
<212> TYPE: PRT
<213> ORGANISM: Artificial sequence
<220> FEATURE:
<223> OTHER INFORMATION: ePDZ construct

<400> SEQUENCE: 6

Ser Gly Thr Ser Pro Glu Leu Gly Phe Ser Ile Ser Gly Gly Val Gly
1               5                   10                  15

Gly Arg Gly Asn Pro Phe Arg Pro Asp Asp Gly Ile Phe Val Thr
            20                  25                  30

Arg Val Gln Pro Glu Gly Pro Ala Ser Lys Leu Leu Gln Pro Gly Asp
        35                  40                  45

Lys Ile Ile Gln Ala Asn Gly Tyr Ser Phe Ile Asn Ile Glu His Gly
50                  55                  60

Gln Ala Val Ser Leu Leu Lys Thr Phe Gln Asn Thr Val Glu Leu Ile
65                  70                  75                  80

Ile Val Arg Glu Val Gly Asn Gly Ala Lys Gln Glu Ile Arg Val Arg
                85                  90                  95

Val Glu Lys Asp Gly Gly Ser Gly Val Ser Val Pro Thr Asn
            100                 105                 110

Leu Glu Val Val Ala Ala Thr Pro Thr Ser Leu Leu Ile Ser Trp Asp
            115                 120                 125

Ala Ser Tyr Tyr Gly Val Ser Tyr Tyr Arg Ile Thr Tyr Gly Glu Thr
        130                 135                 140

Gly Gly Asn Ser Pro Val Gln Glu Phe Thr Val Pro Tyr Ser Ser Ser
145                 150                 155                 160

Thr Ala Thr Ile Ser Gly Leu Lys Pro Gly Val Asp Tyr Thr Ile Thr
                165                 170                 175

Val Tyr Ala Tyr Ser Asp Tyr Tyr Gly Ser His His Tyr Ser Pro Ile
            180                 185                 190

Ser Ile Asn Tyr Arg Thr Ser Gly Cys
        195                 200

<210> SEQ ID NO 7
<211> LENGTH: 349
<212> TYPE: PRT
<213> ORGANISM: Artificial sequence
<220> FEATURE:
<223> OTHER INFORMATION: Chimeric binder construct

<400> SEQUENCE: 7

Gly Gly Val Ala Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
50                  55                  60
```

Ala Gln Glu Trp Cys Arg Lys Tyr Met Lys Ser Gly Asn Val Lys Asp
 65                  70                  75                  80

Leu Thr Gln Ala Trp Asp Leu Tyr Tyr His Val Phe Arg Ile Ser
                 85                  90                  95

Gly Gly Ser Lys Ala Leu Leu Lys Gly Val Arg Asp Phe Asn Pro Ile
            100                 105                 110

Ser Ala Cys Val Cys Leu Leu Glu Asn Ser Ser Asp Gly His Ser Glu
        115                 120                 125

Arg Leu Phe Gly Ile Gly Phe Gly Pro Tyr Ile Ile Ala Asn Gln His
130                 135                 140

Leu Phe Arg Arg Asn Asn Gly Glu Leu Thr Ile Lys Thr Met His Gly
145                 150                 155                 160

Glu Phe Lys Val Lys Asn Ser Thr Gln Leu Gln Met Lys Pro Val Glu
                165                 170                 175

Gly Arg Asp Ile Ile Val Ile Lys Met Ala Lys Asp Phe Pro Pro Phe
            180                 185                 190

Pro Gln Lys Leu Lys Phe Arg Gln Pro Thr Ile Lys Asp Arg Val Cys
        195                 200                 205

Met Val Ser Thr Asn Phe Gln Gln Lys Ser Val Ser Ser Leu Val Ser
210                 215                 220

Glu Ser Ser His Ile Val His Lys Glu Asp Thr Ser Phe Trp Gln His
225                 230                 235                 240

Trp Ile Thr Thr Lys Asp Gly Gln Cys Gly Ser Pro Leu Val Ser Ile
                245                 250                 255

Ile Asp Gly Asn Ile Leu Gly Ile His Ser Leu Thr His Thr Thr Asn
            260                 265                 270

Gly Ser Asn Tyr Phe Val Glu Phe Pro Glu Lys Phe Val Ala Thr Tyr
        275                 280                 285

Leu Asp Ala Ala Asp Gly Trp Cys Lys Asn Trp Lys Phe Asn Ala Asp
290                 295                 300

Lys Ile Ser Trp Gly Ser Phe Ile Leu Trp Glu Asp Ala Pro Glu Asp
305                 310                 315                 320

Phe Met Ser Gly Leu Val Pro Arg Gly Val Gly Arg Glu Tyr Val Arg
                325                 330                 335

Phe Ala Pro Gly Gly Pro Gln Pro Val Asp Ser Trp Val
            340                 345

<210> SEQ ID NO 8
<211> LENGTH: 315
<212> TYPE: PRT
<213> ORGANISM: Artificial sequence
<220> FEATURE:
<223> OTHER INFORMATION: Chimeric construct

<400> SEQUENCE: 8

Gly Thr Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
                20                  25                  30

Glu Asp Gly Lys Lys Phe Asp Ser Ser Arg Asp Arg Asn Lys Pro Phe
            35                  40                  45

Lys Phe Met Leu Gly Lys Gln Glu Val Ile Arg Gly Trp Glu Glu Gly
        50                  55                  60

Val Ala Gln Met Ser Val Gly Gln Arg Ala Lys Leu Thr Ile Ser Pro
65                  70                  75                  80

```
Asp Tyr Ala Tyr Gly Ala Thr Gly His Pro Gly Ile Ile Pro Pro His
                85                  90                  95
Ala Thr Leu Val Phe Asp Val Glu Leu Leu Lys Leu Glu Gly Gly Ser
            100                 105                 110
Gly Gly Ser Gly Gly Ser Pro Glu Leu Gly Phe Ser Ile Ser Gly Gly
        115                 120                 125
Val Gly Gly Arg Gly Asn Pro Phe Arg Pro Asp Asp Gly Ile Phe
    130                 135                 140
Val Thr Arg Val Gln Pro Glu Gly Pro Ala Ser Lys Leu Leu Gln Pro
145                 150                 155                 160
Gly Asp Lys Ile Ile Gln Ala Asn Gly Tyr Ser Phe Ile Asn Ile Glu
                165                 170                 175
His Gly Gln Ala Val Ser Leu Leu Lys Thr Phe Gln Asn Thr Val Glu
            180                 185                 190
Leu Ile Ile Val Arg Glu Val Gly Asn Gly Ala Lys Gln Glu Ile Arg
        195                 200                 205
Val Arg Val Glu Lys Asp Gly Gly Ser Gly Gly Val Ser Ser Val Pro
    210                 215                 220
Thr Asn Leu Glu Val Val Ala Ala Thr Pro Thr Ser Leu Leu Ile Ser
225                 230                 235                 240
Trp Asp Ala Ser Tyr Tyr Gly Val Ser Tyr Tyr Arg Ile Thr Tyr Gly
                245                 250                 255
Glu Thr Gly Gly Asn Ser Pro Val Gln Glu Phe Thr Val Pro Tyr Ser
            260                 265                 270
Ser Ser Thr Ala Thr Ile Ser Gly Leu Lys Pro Gly Val Asp Tyr Thr
        275                 280                 285
Ile Thr Val Tyr Ala Tyr Ser Asp Tyr Tyr Gly Ser His His Tyr Ser
    290                 295                 300
Pro Ile Ser Ile Asn Tyr Arg Thr Ser Gly Cys
305                 310                 315

<210> SEQ ID NO 9
<211> LENGTH: 381
<212> TYPE: PRT
<213> ORGANISM: Artificial sequence
<220> FEATURE:
<223> OTHER INFORMATION: Chimeric construct

<400> SEQUENCE: 9

Gly Gly Ser Gly Gly Ser Gly Gly Val Gln Val Glu Thr Ile Ser Pro
1               5                   10                  15
Gly Asp Gly Arg Thr Phe Pro Lys Arg Gly Gln Thr Cys Val Val His
            20                  25                  30
Tyr Thr Gly Met Leu Glu Asp Gly Lys Lys Phe Asp Ser Ser Arg Asp
        35                  40                  45
Arg Asn Lys Pro Phe Lys Phe Met Leu Gly Lys Gln Glu Val Ile Arg
    50                  55                  60
Gly Trp Glu Glu Gly Val Ala Gln Met Ser Val Gly Gln Arg Ala Lys
65                  70                  75                  80
Leu Thr Ile Ser Pro Asp Tyr Ala Tyr Gly Ala Thr Gly His Pro Gly
                85                  90                  95
Ile Ile Pro Pro His Ala Thr Leu Val Phe Asp Val Glu Leu Leu Lys
            100                 105                 110
Leu Glu Gly Gly Ser Gly Gly Ser Gly Gly Ser Gly Gly Ser Gly Gly
        115                 120                 125
```

```
Ser Gly Gly Ser Lys Ala Leu Leu Lys Gly Val Arg Asp Phe Asn Pro
            130                 135                 140

Ile Ser Ala Cys Val Cys Leu Leu Glu Asn Ser Ser Asp Gly His Ser
145                 150                 155                 160

Glu Arg Leu Phe Gly Ile Gly Phe Gly Pro Tyr Ile Ile Ala Asn Gln
                165                 170                 175

His Leu Phe Arg Arg Asn Asn Gly Glu Leu Thr Ile Lys Thr Met His
            180                 185                 190

Gly Glu Phe Lys Val Lys Asn Ser Thr Gln Leu Gln Met Lys Pro Val
        195                 200                 205

Glu Gly Arg Asp Ile Ile Val Ile Lys Met Ala Lys Asp Phe Pro Pro
210                 215                 220

Phe Pro Gln Lys Leu Lys Phe Arg Gln Pro Thr Ile Lys Asp Arg Val
225                 230                 235                 240

Cys Met Val Ser Thr Asn Phe Gln Gln Lys Ser Val Ser Ser Leu Val
                245                 250                 255

Ser Glu Ser Ser His Ile Val His Lys Glu Asp Thr Ser Phe Trp Gln
            260                 265                 270

His Trp Ile Thr Thr Lys Asp Gly Gln Cys Gly Ser Pro Leu Val Ser
        275                 280                 285

Ile Ile Asp Gly Asn Ile Leu Gly Ile His Ser Leu Thr His Thr Thr
290                 295                 300

Asn Gly Ser Asn Tyr Phe Val Glu Phe Pro Glu Lys Phe Val Ala Thr
305                 310                 315                 320

Tyr Leu Asp Ala Ala Asp Gly Trp Cys Lys Asn Trp Lys Phe Asn Ala
                325                 330                 335

Asp Lys Ile Ser Trp Gly Ser Phe Ile Leu Trp Glu Asp Ala Pro Glu
            340                 345                 350

Asp Phe Met Ser Gly Leu Val Pro Arg Gly Val Gly Arg Glu Tyr Val
        355                 360                 365

Arg Phe Ala Pro Gly Ser Thr His His His His His His
370                 375                 380

<210> SEQ ID NO 10
<211> LENGTH: 355
<212> TYPE: PRT
<213> ORGANISM: Artificial sequence
<220> FEATURE:
<223> OTHER INFORMATION: Chimeric construct

<400> SEQUENCE: 10

Ser Met Ser Thr Ser Gly Ser Gly Ser Gly Ser Ala Lys Gly Ser Val
1               5                   10                  15

Val Ile Val Gly Arg Ile Asn Leu Ser Gly Asp Thr Ala Tyr Ser Gln
                20                  25                  30

Gln Thr Arg Gly Ala Ala Gly Ile Ala Ala Thr Ser Ala Thr Gly Arg
            35                  40                  45

Asp Lys Asn Gln Val Asp Gly Glu Val Gln Val Leu Ser Thr Ala Thr
        50                  55                  60

Gln Ser Phe Leu Ala Thr Cys Val Asn Gly Val Cys Trp Thr Val Tyr
65                  70                  75                  80

His Gly Ala Gly Ser Lys Thr Leu Ala Gly Pro Lys Gly Pro Ile Thr
                85                  90                  95

Gln Met Tyr Thr Asn Val Asp Gln Asp Leu Val Gly Trp Pro Ala Pro
            100                 105                 110
```

```
Pro Gly Ala Arg Ser Met Thr Pro Cys Thr Cys Gly Ser Ser Asp Leu
        115                 120                 125

Tyr Leu Val Thr Arg His Ala Asp Val Ile Pro Val Arg Arg Arg Gly
    130                 135                 140

Asp Ser Arg Gly Ser Leu Leu Ser Pro Arg Pro Val Ser Tyr Leu Lys
145                 150                 155                 160

Gly Ser Ser Gly Gly Pro Leu Leu Cys Pro Ser Gly His Val Val Gly
                165                 170                 175

Ile Phe Arg Ala Ala Val Cys Thr Arg Gly Val Ala Lys Ala Val Asp
                180                 185                 190

Phe Ile Pro Val Glu Ser Met Glu Thr Thr Met Arg Gly Gly Ser Gly
        195                 200                 205

Gly Ser Gly Gly Glu Thr Val Arg Phe Gln Ser Gly Gly Ser Gly Gly
    210                 215                 220

Asp Glu Leu Ile Leu Cys Pro Leu Asp Leu Gly Gly Ser Gly Gly Ser
225                 230                 235                 240

Gly Gly Ser Gly Gly Ser Gly Gly Ser Gly Gly Val Ala Ile Leu
                245                 250                 255

Trp His Glu Met Trp His Glu Gly Leu Glu Glu Ala Ser Arg Leu Tyr
                260                 265                 270

Phe Gly Glu Arg Asn Val Lys Gly Met Phe Glu Val Leu Glu Pro Leu
        275                 280                 285

His Ala Met Met Glu Arg Gly Pro Gln Thr Leu Lys Glu Thr Ser Phe
    290                 295                 300

Asn Gln Ala Tyr Gly Arg Asp Leu Met Glu Ala Gln Glu Trp Cys Arg
305                 310                 315                 320

Lys Tyr Met Lys Ser Gly Asn Val Lys Asp Leu Thr Gln Ala Trp Asp
                325                 330                 335

Leu Tyr Tyr His Val Phe Arg Arg Ile Gly Gly Thr Gly His His His
                340                 345                 350

His His His
        355

<210> SEQ ID NO 11
<211> LENGTH: 286
<212> TYPE: PRT
<213> ORGANISM: Artificial sequence
<220> FEATURE:
<223> OTHER INFORMATION: Chimeric construct

<400> SEQUENCE: 11

Met Ala His His His His His His Ser Ser Gly Gly Ser Pro Pro Pro
1               5                   10                  15

Pro Leu Pro Pro Lys Arg Arg Gly Gly Ser Gly Ser Gly Gly
            20                  25                  30

Val Ser Lys Gly Glu Glu Leu Phe Thr Gly Val Val Pro Ile Leu Val
            35                  40                  45

Glu Leu Asp Gly Asp Val Asn Gly His Lys Phe Ser Val Ser Gly Glu
        50                  55                  60

Gly Glu Gly Asp Ala Thr Tyr Gly Lys Leu Thr Leu Lys Phe Ile Cys
65                  70                  75                  80

Thr Thr Gly Lys Leu Pro Val Pro Trp Pro Thr Leu Val Thr Thr Leu
                85                  90                  95

Thr Tyr Gly Val Gln Cys Phe Ser Arg Tyr Pro Asp His Met Lys Gln
                100                 105                 110
```

His Asp Phe Phe Lys Ser Ala Met Pro Glu Gly Tyr Val Gln Glu Arg
            115                 120                 125

Thr Ile Phe Phe Lys Asp Asp Gly Asn Tyr Lys Thr Arg Ala Glu Val
        130                 135                 140

Lys Phe Glu Gly Asp Thr Leu Val Asn Arg Ile Glu Leu Lys Gly Ile
145                 150                 155                 160

Asp Phe Lys Glu Asp Gly Asn Ile Leu Gly His Lys Leu Glu Tyr Asn
                165                 170                 175

Tyr Asn Ser His Asn Val Tyr Ile Met Ala Asp Lys Gln Lys Asn Gly
            180                 185                 190

Ile Lys Val Asn Phe Lys Ile Arg His Asn Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Met Val Leu Leu Glu Phe Val
                245                 250                 255

Thr Ala Ala Gly Ile Thr Leu Gly Met Asp Glu Leu Tyr Lys Gly Gly
            260                 265                 270

Ser Gly Gly Ser Gly Gly Pro Gln Pro Val Asp Ser Trp Val
        275                 280                 285

<210> SEQ ID NO 12
<211> LENGTH: 114
<212> TYPE: PRT
<213> ORGANISM: Artificial sequence
<220> FEATURE:
<223> OTHER INFORMATION: Chimeric construct

<400> SEQUENCE: 12

Met Glu Asn Ala Gln Lys Gly Glu Ile Met Pro Asn Ile Pro Gln Met
1               5                   10                  15

Ser Ala Phe Trp Tyr Ala Val Arg Thr Ala Val Ile Asn Ala Ala Ser
            20                  25                  30

Gly Arg Gln Thr Val Asp Glu Ala Leu Lys Asp Ala Gln Thr Asn Ser
        35                  40                  45

Ser Ser Asn Asn Asn Asn Asn Asn Asn Asn Asn Leu Gly Ile Glu
    50                  55                  60

Gly Arg Gly Glu Asn Leu Tyr Phe Gln Ser Gly His His His His
65                  70                  75                  80

His His Gly Gly Ser Gly Gly Pro Pro Pro Leu Pro Pro Lys Arg
            85                  90                  95

Arg Arg Gly Gly Ser Gly Gly Ser Gly Gly Pro Gln Pro Val Asp Ser
                100                 105                 110

Trp Val

<210> SEQ ID NO 13
<211> LENGTH: 24
<212> TYPE: PRT
<213> ORGANISM: Artificial sequence
<220> FEATURE:
<223> OTHER INFORMATION: Chimeric peptide

<400> SEQUENCE: 13

Pro Pro Pro Pro Leu Pro Pro Lys Arg Arg Arg Gly Gly Ser Gly Gly
1               5                   10                  15

Pro Gln Pro Val Asp Ser Trp Val
            20

<210> SEQ ID NO 14
<211> LENGTH: 406
<212> TYPE: PRT
<213> ORGANISM: Artificial sequence
<220> FEATURE:
<223> OTHER INFORMATION: Chimeric construct

<400> SEQUENCE: 14

Met Glu Asn Ala Gln Lys Gly Glu Ile Met Pro Asn Ile Pro Gln Met
1               5                   10                  15

Ser Ala Phe Trp Tyr Ala Val Arg Thr Ala Val Ile Asn Ala Ala Ser
            20                  25                  30

Gly Arg Gln Thr Val Asp Glu Ala Leu Lys Asp Ala Gln Thr Asn Ser
        35                  40                  45

Ser Ser Asn Asn Asn Asn Asn Asn Asn Asn Asn Asn Leu Gly Ile Glu
    50                  55                  60

Gly Arg Gly Asp Asp Val Thr Pro Cys Ser Met Ser Thr Ser Gly Ser
65                  70                  75                  80

Gly Gly Ala Glu Tyr Val Arg Ala Leu Phe Asp Phe Asn Gly Asn Asp
                85                  90                  95

Glu Glu Asp Leu Pro Phe Lys Lys Gly Asp Ile Leu Arg Ile Arg Asp
            100                 105                 110

Lys Pro Glu Glu Gln Trp Trp Asn Ala Glu Asp Ser Glu Gly Lys Arg
        115                 120                 125

Gly Met Ile Pro Val Pro Tyr Val Glu Lys Tyr Arg Pro Ala Ser Ala
130                 135                 140

Ser Val Ser Ala Leu Ile Gly Gly Arg Gly Ser Gly Gly Ser Gly
145                 150                 155                 160

Gly Ser Gly Gly Ser Gly Gly Ser Gly Gly Ser Ala Lys Gly Ser Val
                165                 170                 175

Val Ile Val Gly Arg Ile Asn Leu Ser Gly Asp Thr Ala Tyr Ser Gln
            180                 185                 190

Gln Thr Arg Gly Ala Ala Gly Ile Ala Ala Thr Ser Ala Thr Gly Arg
        195                 200                 205

Asp Lys Asn Gln Val Asp Gly Glu Val Gln Val Leu Ser Thr Ala Thr
    210                 215                 220

Gln Ser Phe Leu Ala Thr Cys Val Asn Gly Val Cys Trp Thr Val Tyr
225                 230                 235                 240

His Gly Ala Gly Ser Lys Thr Leu Ala Gly Pro Lys Gly Pro Ile Thr
                245                 250                 255

Gln Met Tyr Thr Asn Val Asp Gln Asp Leu Val Gly Trp Pro Ala Pro
            260                 265                 270

Pro Gly Ala Arg Ser Met Thr Pro Cys Thr Cys Gly Ser Ser Asp Leu
        275                 280                 285

Tyr Leu Val Thr Arg His Ala Asp Val Ile Pro Val Arg Arg Arg Gly
    290                 295                 300

Asp Ser Arg Gly Ser Leu Leu Ser Pro Arg Pro Val Ser Tyr Leu Lys
305                 310                 315                 320

Gly Ser Ser Gly Gly Pro Leu Leu Cys Pro Ser Gly His Val Val Gly
                325                 330                 335

Ile Phe Arg Ala Ala Val Cys Thr Arg Gly Val Ala Lys Ala Val Asp
            340                 345                 350

```
Phe Ile Pro Val Glu Ser Met Glu Thr Thr Met Arg Gly Gly Gly
        355                 360                 365
Ser Gly Gly Glu Thr Val Arg Phe Gln Ser Gly Ser Gly Gly Asp
    370                 375                 380
Glu Leu Ile Leu Cys Pro Leu Asp Leu Gly Gly Ser Gly Thr Gly
385                 390                 395                 400
His His His His His
            405

<210> SEQ ID NO 15
<211> LENGTH: 439
<212> TYPE: PRT
<213> ORGANISM: Artificial sequence
<220> FEATURE:
<223> OTHER INFORMATION: Chimeric construct

<400> SEQUENCE: 15

Met Glu Asn Ala Gln Lys Gly Glu Ile Met Pro Asn Ile Pro Gln Met
1               5                   10                  15
Ser Ala Phe Trp Tyr Ala Val Arg Thr Ala Val Ile Asn Ala Ala Ser
            20                  25                  30
Gly Arg Gln Thr Val Asp Glu Ala Leu Lys Asp Ala Gln Thr Asn Ser
        35                  40                  45
Ile Thr Ser Leu Tyr Lys Lys Ala Gly Ser Glu Thr Val Arg Phe Gln
    50                  55                  60
Ser Gly Gly Ser Gly Gly Ser Met Glu Ile Arg Val Arg Val Glu Lys
65                  70                  75                  80
Asp Pro Glu Leu Gly Phe Ser Ile Ser Gly Gly Val Gly Gly Arg Gly
                85                  90                  95
Asn Pro Phe Arg Pro Asp Asp Gly Ile Phe Val Thr Arg Val Gln
            100                 105                 110
Pro Glu Gly Pro Ala Ser Lys Leu Leu Gln Pro Gly Asp Lys Ile Ile
        115                 120                 125
Gln Ala Asn Gly Tyr Ser Phe Ile Asn Ile Glu His Gly Gln Ala Val
130                 135                 140
Ser Leu Leu Lys Thr Phe Gln Asn Thr Val Glu Leu Ile Ile Val Arg
145                 150                 155                 160
Glu Val Ser Ser Gly Gly Arg Gly Gly Ser Gly Gly Ser Gly Gly Ser
                165                 170                 175
Gly Gly Ser Gly Gly Ser Gly Gly Ser Ser Lys Ala Leu Leu Lys Gly
            180                 185                 190
Val Arg Asp Phe Asn Pro Ile Ser Ala Cys Val Cys Leu Leu Glu Asn
        195                 200                 205
Ser Ser Asp Gly His Ser Glu Arg Leu Phe Gly Ile Gly Phe Gly Pro
210                 215                 220
Tyr Ile Ile Ala Asn Gln His Leu Phe Arg Arg Asn Asn Gly Glu Leu
225                 230                 235                 240
Thr Ile Lys Thr Met His Gly Glu Phe Lys Val Lys Asn Ser Thr Gln
                245                 250                 255
Leu Gln Met Lys Pro Val Glu Gly Arg Asp Ile Ile Val Ile Lys Met
            260                 265                 270
Ala Lys Asp Phe Pro Pro Phe Pro Gln Lys Leu Lys Phe Arg Gln Pro
        275                 280                 285
Thr Ile Lys Asp Arg Val Cys Met Val Ser Thr Asn Phe Gln Gln Lys
290                 295                 300
```

```
Ser Val Ser Ser Leu Val Ser Glu Ser His Ile Val His Lys Glu
305                 310                 315                 320

Asp Thr Ser Phe Trp Gln His Trp Ile Thr Thr Lys Asp Gly Gln Cys
                325                 330                 335

Gly Ser Pro Leu Val Ser Ile Ile Asp Gly Asn Ile Leu Gly Ile His
            340                 345                 350

Ser Leu Thr His Thr Thr Asn Gly Ser Asn Tyr Phe Val Glu Phe Pro
        355                 360                 365

Glu Lys Phe Val Ala Thr Tyr Leu Asp Ala Ala Asp Gly Trp Cys Lys
    370                 375                 380

Asn Trp Lys Phe Asn Ala Asp Lys Ile Ser Trp Gly Ser Phe Ile Leu
385                 390                 395                 400

Trp Glu Asp Ala Pro Glu Ser Gly Gly Asp Glu Met Glu Glu Cys Ala
                405                 410                 415

Ser His Leu Gly Ser Gly Arg Glu Tyr Val Arg Phe Ala Pro Gly Ser
            420                 425                 430

Thr His His His His His His
        435
```

<210> SEQ ID NO 16
<211> LENGTH: 24
<212> TYPE: PRT
<213> ORGANISM: Artificial sequence
<220> FEATURE:
<223> OTHER INFORMATION: Synthetic peptide

<400> SEQUENCE: 16

```
Arg Trp Lys Lys Asn Phe Ile Ala Val Ser Ala Ala Asn Arg Phe Lys
1               5                   10                  15

Lys Ile Ser Ser Ser Gly Ala Leu
            20
```

<210> SEQ ID NO 17
<211> LENGTH: 8
<212> TYPE: PRT
<213> ORGANISM: Artificial sequence
<220> FEATURE:
<223> OTHER INFORMATION: Synthetic peptide

<400> SEQUENCE: 17

```
Pro Gln Pro Val Asp Ser Trp Val
1               5
```

<210> SEQ ID NO 18
<211> LENGTH: 8
<212> TYPE: PRT
<213> ORGANISM: Artificial sequence
<220> FEATURE:
<223> OTHER INFORMATION: Synthetic peptide

<400> SEQUENCE: 18

```
Pro Ala Ser Pro Asp Ser Trp Val
1               5
```

<210> SEQ ID NO 19
<211> LENGTH: 10
<212> TYPE: PRT
<213> ORGANISM: Artificial sequence
<220> FEATURE:
<223> OTHER INFORMATION: Synthetic peptide

<400> SEQUENCE: 19

```
Arg Glu Thr Val Arg Phe Gln Ser Asp Thr
1               5                   10

<210> SEQ ID NO 20
<211> LENGTH: 10
<212> TYPE: PRT
<213> ORGANISM: Artificial sequence
<220> FEATURE:
<223> OTHER INFORMATION: Synthetic peptide

<400> SEQUENCE: 20

Asp Glu Leu Ile Leu Cys Pro Leu Asp Leu
1               5                   10
```

The invention claimed is:

1. A biosensor that comprises first and second molecular components wherein: the first molecular component comprises: a first binding partner, a protease amino acid sequence and an inhibitor of the protease activity of said protease; and the second molecular component comprises: a second binding partner and a subcomponent capable of facilitating: (i) at least partial release of inhibition of the protease of the first molecular component by the inhibitor to switch the protease of the first molecular component from a protease inactive to a protease active state; or (ii) at least partial inhibition of the protease of the first molecular component by the inhibitor to switch the protease of the first molecular component from a protease active to a protease inactive state; upon a binding interaction between the first and second binding partners.

2. The biosensor of claim 1, wherein the first binding partner and the second binding partner are capable of directly binding, coupling, interacting or forming a complex to thereby co-localize the first molecular component and the second molecular component.

3. The biosensor of claim 1, wherein the first binding partner and the second binding partner are capable of binding, coupling, interacting or forming a complex with a target molecule to thereby co-localize the first molecular component and the second molecular component.

4. The biosensor of claim 3, wherein the first binding partner and the second binding partner are capable of binding, interacting or forming a complex with the same target molecule to thereby co-localize the first molecular component and the second molecular component.

5. The biosensor of claim 3, wherein the first binding partner and the second binding partner are capable of co-operatively binding the target molecule.

6. The biosensor of claim 1, wherein the subcomponent of the second molecular component comprises an amino acid sequence of a protein or fragment thereof.

7. The biosensor of claim 6, wherein the protein or fragment thereof is not a protease or protease fragment.

8. The biosensor of claim 7, wherein the first molecular component comprises a cross-binder that is capable of binding the protein or protein fragment that is not a protease.

9. The biosensor of claim 8, wherein the cross-binder is coupled, fused, connected or contiguous with the inhibitor of the protease activity of the first molecular component.

10. The biosensor of claim 9, wherein upon a binding interaction between the first binding partner, the second binding partner and optionally, a target molecule, the cross-binder is capable of binding the protein of the second molecular component to thereby at least partly release inhibition of the protease of the first molecular component by the inhibitor to thereby switch the protease of the first molecular component from a protease inactive to a protease active state.

11. The biosensor of claim 7, wherein the protein is, or comprises calmodulin or a fragment thereof.

12. The biosensor of claim 11, wherein the cross-binder is a peptide capable of binding of interacting with calmodulin.

13. The biosensor of claim 7, wherein the protein is, or comprises, an affinity clamp; wherein the affinity clamp comprises a recognition domain and wherein the recognition domain is capable of binding one or more target molecules.

14. The biosensor of claim 13, wherein the cross-binder is a peptide capable of binding or interacting with the affinity clamp.

15. The biosensor of claim 13, wherein the affinity clamp further comprises an enhancer domain.

16. The biosensor of claim 15, wherein the recognition domain is a PDZ domain.

17. The biosensor of claim 1, wherein the first binding partner and/or the second binding partner is or comprises an antibody or antibody fragment.

18. The biosensor of claim 1, wherein the first binding partner and/or the second binding partner is or comprises one or a plurality of epitopes.

19. The biosensor of claim 1, wherein the subcomponent of the second molecular component comprises an amino acid sequence of another protease or protease fragment.

20. The biosensor of claim 19, wherein the first molecular component further comprises at least one protease cleavage site cleavable by said another protease of the second molecular component to at least partly release inhibition of the protease of the first molecular component by the inhibitor and thereby switch the first molecular component of the biosensor from a protease inactive to a protease active state.

21. The biosensor of claim 20, wherein the second molecular component does not comprise an inhibitor of said another protease.

22. The biosensor of claim 21, wherein the second molecular component further comprises at least one protease cleavage site cleavable by the protease of the first molecular component and an inhibitor of said another protease, whereby cleavage of the protease cleavage site of the second molecular component by the protease of the first molecular component at least partly releases inhibition of said another protease by the inhibitor to thereby switch the second molecular component of the biosensor from a protease inactive to a protease active state.

23. The biosensor of claim 1, wherein the protease of the first molecular component and/or the second molecular component is a cysteine protease, a serine protease, an aspartate protease, a metalloprotease, a threonine protease, or a glutamic acid protease.

24. The biosensor of claim 23, wherein the protease is derived or obtainable from a virus.

25. The biosensor of claim 24, wherein the virus is a Potyvirus or a Flavivirus.

26. The biosensor of claim 25, wherein the Potyvirus is SMV, TEV or TVMV.

27. The biosensor of claim 26, wherein the Flaivivirus is HCV.

28. The biosensor of claim 27, wherein the protease is an NIa protease.

29. The biosensor of claim 1, wherein the inhibitor of the protease of the first molecular component and/or the second molecular component is a peptide.

30. The biosensor of claim 29, wherein the inhibitor is an autoinhibitory peptide.

31. The biosensor of claim 30, wherein the autoinhibitory peptide is encoded by a Potyvirus genome or a Flavivirus genome.

32. The biosensor of claim 1, wherein: (a) the first molecular component comprises an amino acid sequence set forth in any one of SEQ ID Nos: 1-10; and/or (b) the second molecular component comprises an amino acid sequence set forth in any one of SEQ ID Nos: 1-10.

33. A composition or kit comprising the biosensor of claim 1 and a substrate.

34. The composition or kit of claim 33, wherein the substrate comprises an amino acid sequence cleavable by the protease of the biosensor.

35. The composition or kit of claim 33, further comprising an amplifier molecule.

36. The composition or kit of claim 35, wherein the amplifier molecule comprises: (i) an amino acid sequence of a protease that is different to the protease(s) of the biosensor; (ii) an inhibitor of the protease of (i); and (iii) a linker amino acid sequence which comprises a cleavage site for the protease of the biosensor.

37. The composition or kit of claim 35, wherein the amplifier molecule comprises a biosensor interacting domain for linking or coupling the amplifier molecule to the biosensor.

38. The composition or kit of claim 33, wherein the substrate comprises an amino acid sequence cleavable by the protease of the amplification molecule.

39. A method of detecting a target molecule, said method including the step of contacting the composition of claim 33 with a sample to thereby determine the presence or absence of a target molecule in the sample.

40. A method of diagnosis of a disease in an organism, said method including the step of contacting the composition of claim 33 with a biological sample obtained from the organism to thereby determine the presence or absence of a target molecule in the biological sample, determination of the presence or absence of the target molecule facilitating diagnosis of the disease.

41. The method of claim 40, wherein the organism is an animal.

42. The method of claim 41, wherein the animal is a human or other mammal.

43. An isolated nucleic acid encoding the first molecular component of the second molecular component of the biosensor of claim 1.

44. A genetic construct comprising the isolated nucleic acid of claim 43.

45. A host cell comprising the genetic construct of claim 44.

* * * * *